United States Patent
Schoenmeyer et al.

(10) Patent No.: US 9,741,112 B2
(45) Date of Patent: Aug. 22, 2017

(54) GENERATING IMAGE-BASED DIAGNOSTIC TESTS BY OPTIMIZING IMAGE ANALYSIS AND DATA MINING OF CO-REGISTERED IMAGES

(71) Applicants: Ralf Schoenmeyer, Gilching (DE); Gerd Binnig, Kottgeisering (DE); Guenter Schmidt, Munich (DE)

(72) Inventors: Ralf Schoenmeyer, Gilching (DE); Gerd Binnig, Kottgeisering (DE); Guenter Schmidt, Munich (DE)

(73) Assignee: Definiens AG, Munich (DE)

( * ) Notice: Subject to any disclaimer, the term of this patent is extended or adjusted under 35 U.S.C. 154(b) by 230 days.

(21) Appl. No.: 14/850,436

(22) Filed: Sep. 10, 2015

(65) Prior Publication Data

US 2017/0076442 A1    Mar. 16, 2017

(51) Int. Cl.
*G06K 9/00* (2006.01)
*G06T 7/00* (2017.01)
(Continued)

(52) U.S. Cl.
CPC ........ *G06T 7/0012* (2013.01); *G06F 19/3443* (2013.01); *G06T 7/11* (2017.01);
(Continued)

(58) Field of Classification Search
CPC ................ G06T 11/206; G06T 7/0012; G06T 2207/10061; G06T 2207/20016; G06T 2207/20021; G06T 2207/20221
See application file for complete search history.

(56) References Cited

U.S. PATENT DOCUMENTS

2004/0064037 A1* 4/2004 Smith .................. G06T 7/0012
                                                   600/420
2005/0190955 A1* 9/2005 Brown .................. G01R 33/56
                                                   382/128
(Continued)

FOREIGN PATENT DOCUMENTS

WO    WO2008/080403    7/2008

OTHER PUBLICATIONS

Athelogou et al., "Kontextbasierte Bildanalyse mit Cognition Networks," Biospektrum, Jun. 1, 2007 pp. 657-659 XP055056406 (3 pages).
(Continued)

*Primary Examiner* — Amara Abdi
(74) *Attorney, Agent, or Firm* — Imperium Patent Works; Darien K. Wallace

(57) ABSTRACT

A method for generating an image-based test improves diagnostic accuracy by iteratively modifying rule sets governing image and data analysis of coregistered image tiles. Digital images of stained tissue slices are divided into tiles, and tiles from different images are coregistered. First image objects are linked to selected pixels of the tiles. First numerical data is generated by measuring the first objects. Each pixel of a heat map aggregates first numerical data from coregistered tiles. Second objects are linked to selected pixels of the heat map. Measuring the second objects generates second numerical data. The method improves how well second numerical data correlates with clinical data of the patient whose tissue is analyzed by modifying the rule sets used to generate the first and second objects and the first and second numerical data. The test is defined by those rule sets that produce the best correlation with the clinical data.

20 Claims, 30 Drawing Sheets

(51) Int. Cl.
*G06F 19/00* (2011.01)
*G06T 7/11* (2017.01)
*G06T 7/162* (2017.01)
*G06T 11/20* (2006.01)

(52) U.S. Cl.
CPC ............ *G06T 7/162* (2017.01); *G06T 11/206* (2013.01); *G06T 2200/04* (2013.01); *G06T 2207/10056* (2013.01); *G06T 2207/20016* (2013.01); *G06T 2207/20021* (2013.01); *G06T 2207/20081* (2013.01); *G06T 2207/30024* (2013.01)

(56) References Cited

U.S. PATENT DOCUMENTS

| | | | | |
|---|---|---|---|---|
| 2008/0144013 A1* | 6/2008 | Lanoue | ................ | G01J 3/02 356/73 |
| 2008/0240613 A1* | 10/2008 | Dietz | .................. | G02B 21/365 382/284 |
| 2010/0215227 A1* | 8/2010 | Grunkin | ................ | G06F 19/321 382/128 |
| 2010/0265267 A1* | 10/2010 | Schaepe | ............. | G06K 9/00637 345/619 |
| 2012/0127297 A1* | 5/2012 | Baxi | ..................... | G06T 7/0002 348/79 |
| 2014/0228707 A1* | 8/2014 | Brieu | ....................... | A61B 5/00 600/567 |

OTHER PUBLICATIONS

Baum et al., "Investigation of PET/MRI image fusion schemes for enhanced breast cancer diagnosis," IEEE Nuclear Science Symposium Conference Record, Oct. 1, 2007 pp. 3774-3780 XP031206429 (7 pages).

Extended European Search Report dated Apr. 2, 2013 in European patent application 12176077.1 (published as EP2546802) (9 pages).

* cited by examiner

GENERATING IMAGE-BASED DIAGNOSTIC TESTS BY OPTIMIZING IMAGE ANALYSIS AND DATA MINING OF CO-REGISTERED IMAGES

CROSS REFERENCE TO RELATED APPLICATIONS

This application is a continuation of, and claims priority under 35 U.S.C. §120 from, nonprovisional U.S. patent application Ser. No. 14/197,197 entitled "Generating Image-Based Diagnostic Tests By Optimizing Image Analysis and Data Mining Of Co-Registered Images," filed on Mar. 4, 2014, now U.S. Pat. No. 9,159,129. Application Ser. No. 14/197,197, in turn, is a continuation-in-part of, and claims the benefit under 35 U.S.C. §120 from, nonprovisional U.S. patent application Ser. No. 13/546,182, entitled "Generating Artificial Hyperspectral Images Using Correlated Analysis of Co-Registered Images", filed on Jul. 11, 2012, now U.S. Pat. No. 8,699,769. Application Ser. No. 13/546,182, in turn, claims the benefit under 35 U.S.C. §119 of provisional application Ser. No. 61/572,221, entitled "Generating Artificial Hyper-Spectral Images by Co-Analysis of Co-Registered Images", filed on Jul. 12, 2011. The subject matter of each of the foregoing documents is incorporated herein by reference.

TECHNICAL FIELD

The present invention relates to generating diagnostic tests by optimizing image analysis and data mining of coregistered tissue slices of patients.

BACKGROUND

A method for generating artificial hyperspectral images can be performed by transforming a new problem into an old one that has already been solved. The problem of how to extract valuable information from coregistered tissue slices can be solved by transforming this problem into an image analysis problem that can be performed with existing techniques. The new problem concerns how to correlate local object-based image analysis results from different tissue slices taken from the same tissue of a given patient. The correlated analysis (co-analysis) results in a much higher quality of the medical evaluation than what a "slide-after-slide analysis" could provide.

A method is sought for extracting valuable information from many high resolution images of adjacent tissue slices that reduces the computing resources required to analyze the large amount of information associated with any particular x-y position in coregistered images.

SUMMARY

High-resolution digital images of adjacent slices of a tissue sample are acquired, and tiles are defined in the images. Values associated with image objects detected in each tile are calculated. The tiles in adjacent images are coregistered. A first hyperspectral image is generated using a first image, and a second hyperspectral image is generated using a second image. A first pixel of the first hyperspectral image has a first pixel value corresponding to a local value obtained using image analysis on a tile in the first image. A second pixel of the second hyperspectral image has a second pixel value corresponding to a local value calculated from a tile in the second image. A third hyperspectral image is generated by combining the first and second hyperspectral images. The third hyperspectral image is then displayed on a computer monitor using a false-color encoding generated using the first and second pixel values An artificial hyper-spectral image is generated from coregistered tissue slides and enables the sophisticated co-analysis of image stacks. Coregistration is performed on tiles of high-resolution images of tissue slices, and image-object statistics are used to generate pixels of a down-scaled hyper-spectral image. The method of analyzing digital images to generate hyperspectral images combines two hyperspectral images to generate a third hyperspectral image.

Digital images of adjacent slices of a tissue sample are first acquired, and first and second tiles of first and second digital images are defined. A first value associated with image objects detected in the first tile is calculated, and a second value associated with image objects detected in the second tile is calculated. The first tile is coregistered with the second tile using the image objects in the first tile and the image objects in the second tile. A first hyperspectral image is generated using the first digital image, and a second hyperspectral image is generated using the second digital image. A first pixel of the first hyperspectral image has a first pixel value and a first pixel location. The first pixel value corresponds to the first value, and the first pixel location in the first hyperspectral image corresponds to the position of the first tile in the first digital image. A second pixel of the second hyperspectral image has a second pixel value corresponding to the second value and a second pixel location corresponding to the position of the second tile. The third hyperspectral image is generated by combining the first and second hyperspectral images.

Image analysis is used to generate image objects by segmenting the third hyperspectral image. Values of properties of the image objects of the third hyperspectral image are determined, and the values are stored in non-volatile memory. The third hyperspectral image is then displayed on a computer monitor using a false-color encoding of the first and second pixel values.

The first value can be calculated using a factor, such as a mean, a median, a minimum, a maximum, a quantile, or a standard deviation of a property of a subset of the image objects detected in the first tile. For example, the first value is calculated using a distance weighted mean of a property of the subset of image objects detected in the first tile, and the distance weighted mean is based on distances from a center of the first tile to a center of each of the image objects in the subset. Where the tissue sample is taken from a patient with cancer, the probability of recurrence of the cancer can be determined based on the first value. A therapy response for the patient can also be generated based on the first value. The first value can also be calculated using the property of those image objects detected in tiles adjacent to the first tile. For example, the subset of the image objects detected in the first tile are those image objects classified as nuclei of tumor cells, and the property is an intensity of staining of the subset of the image objects.

In one embodiment, the tiles are not coregistered with one another, but rather the first hyperspectral image is coregistered with the second hyperspectral image. In another embodiment, the first slice is stained with a first biomarker, and the first value corresponds to a histopathological score of the first biomarker. The second slice is stained with a second biomarker, and the second value corresponds to a histopathological score of the second biomarker. The false-color encoding of the third hyperspectral image is based on the difference between the first value and the second value. The third hyperspectral image thereby depicts the heterogeneity of a tumor in the tissue sample. For example, the first slice is stained with an H&E biomarker, and the first value corresponds to the number of mitotic objects in the first tile that are stained by the H&E biomarker. Alternatively, the first slice is immunohistochemically (IHC) stained using a progesterone receptor antibody, and the first value corresponds to a first Allred score. The second slice is immunohistochemically (IHC) stained using an estrogen receptor antibody, and the second value corresponds to a second Allred score. Alternatively, the second slice is processed with in-situ hybridization, and the second value indicates gene amplification.

In another embodiment, when the user selects a pixel of the third hyperspectral image, a tile of the first digital image that corresponds to the selected pixel of the third hyperspectral image is displayed on the computer monitor. The pixel value can be displayed next to the tile as a numerical value or as part of a bar chart. Similarly, when the user selects the first tile of the first digital image, the corresponding pixel of the third hyperspectral image is highlighted on the computer monitor.

In yet another embodiment, both the full-resolution first digital image and the combined third hyperspectral image are simultaneously displayed on the computer monitor. The tile is outlined on the full-resolution image as the user moves the tip of the cursor arrow over the corresponding pixel of the combined hyperspectral image. A biomarker score value for the tile is displayed next to the tile. As the user points the cursor to a different pixel of the combined hyperspectral image, the tile outline in the full-resolution image moves to the corresponding tile, and the biomarker score value changes to reflect the results of the image analysis at the new tile. The user can navigate to the most critical tiles in the full-resolution first digital image by looking for a particular color of pixels in the combined third hyperspectral image.

A method for generating image-based diagnostic tests improves diagnostic accuracy by iteratively modifying the rule sets that govern how image analysis and data mining is performed. Slices of tissue of a patient are stained with various biomarkers, such as H&E and PHH3. Digital images of the tissue slices are acquired, and the images are divided into tiles. Tiles that are obtained from images of different tissue slices are coregistered with each other to form a stack of tiles. First objects are generated that are linked to pixels of the tiles. A first rule set defines which pixels are linked to each of the first objects. A second rule set is used to generate first numerical data by measuring a first characteristic of the first objects located within each of the tiles.

A heat map is generated by aggregating the first numerical data associated with each stack of tiles. Each stack of tiles is used to generate a pixel of the heat map. Second objects are generated from the heat map. A third rule set defines which pixels of the heat map are linked to each of the second objects. A fourth rule set is used to generate second numerical data by measuring a second characteristic of the second objects detected in the heat map. The method determines how well the second numerical data correlates with actual clinical data for the patient. How well the second numerical data correlates with the actual clinical data for the patient is improved by modifying the first rule set, the second rule set, the third rule set and the fourth rule set and then repeating the steps of generating the first objects, the first numerical data, the second objects and the second numerical data. The method then defines an image-based diagnostic test based on the first rule set, the second rule set, the third rule set and the fourth rule set.

In another embodiment, how well the second numerical data correlates with the actual clinical data for the patient is improved by modifying only the fourth rule set and then repeating the generating of the second numerical data. The heat map and the second objects are displayed on the graphical user interface of the system that generates the image-based diagnostic tests. Examples of image-based diagnostic tests that are defined by the rule sets are an improved immunoscore, Allred score, Gleason score, Elston-Ellis score and HercepTest score. For example, the method generates an image-based diagnostic test that predicts the disease free survival time and the overall survival time of the patient whose tissue samples are being analyzed. The second numerical data correlates well with the actual clinical data for the patient when the actual survival time of the patient equals the survival time of the patient predicted by the image-based diagnostic test.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Figure 1:
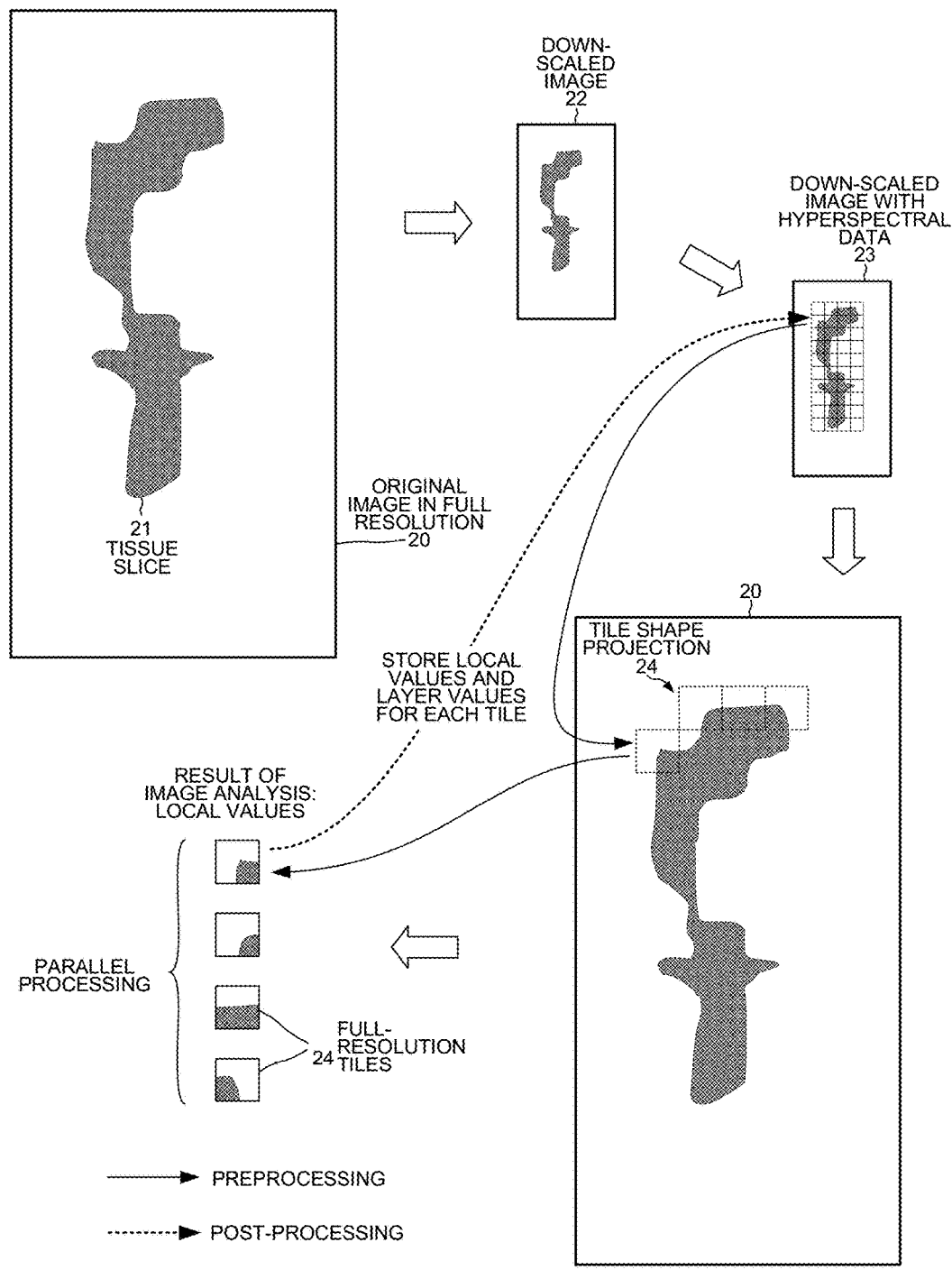
FIG. 1 is a diagram illustrating the production and processing of high-resolution tiles from a master image of a tissue slice.

Reference will now be made in detail to some embodiments of the invention, examples of which are illustrated in the accompanying drawings.

A correlated image analysis is performed on different tissue slices that are stained differently and that thus carry different kinds of information. If the different slices are taken from the tissue in a way that the spacing between the slices is small, it is possible to coregister the slices. The type of tissue that is visible at the same x-y position in adjacent slices might be very similar. In particular, a cancer region in one slice might be visible in a similar way in adjacent slices. When those slices are coregistered, in each x-y position of the slices a feature vector with N features is extracted using image analysis. In order to simplify explaining the principles behind the method, we assume that the number of features is the same for each of the slices. However, the number of features extracted from different slices could be different, and also different features could be extracted from different slices. The features make up a fingerprint of the local tissue properties. If n slices are now coregistered, for each x-y position the N different feature vectors are combined into a new feature vector with n*N features. The combined tissue fingerprint with n*N features for each x-y position is much more meaningful than the sum of the fingerprints of individual tissue slices. In particular, heterogeneity of tumors can be detected with higher precision based on the n*N features for each x-y position of the tissue slices. In an individual slice, different cancer regions might appear in a very similar manner. In a second individual slice, those different cancer regions also might look very similar. In a combined analysis, however, a strong heterogeneity might become evident because highlighted cancer regions might appear at different x-y locations for different stains.

The new problem of how to extract valuable information from coregistered tissue slices is not trivial because a pixel-by-pixel co-analysis of multiple coregistered slices results in an extremely complex analysis that is very difficult to execute if all of the complex properties in the different slices are taken into account. Moreover, if only properties of pixels as opposed to properties of segmented objects are used in the image analysis, the most important and interesting features are lost. The new multi-slice analysis method solves this problem in an efficient way with high quality results by reducing the complexity of the comprehensive multi-slice image analysis without losing relevant information.

The novel method builds upon existing high-quality context-driven image analysis, such as the analysis performed by the Cognition Network Technology (CNT) of Definiens AG. The more complex the images are, the more difficult the image analysis becomes. At the same time, however, the information extracted can be extremely valuable for complex images, such as images of H&E stained slices.

The n different slices are segmented, preferable into square tiles. The tiles then represent smaller regions of downscaled images, down to the size of a pixel. When combined, the downscaled regions form a new image of a much smaller size but with multiple image layers as opposed to the single layer of the original tiled image. The downscaled image with multiple image layers is referred to as a hyperspectral image or a heat map. Information contained in the n slices is thus compressed into one smaller image with many layers. The values within the different layers of the hyperspectral image are generated by statistical analysis of the results from image analysis on the tiles of the different slices.

The results of the image analysis can be represented in multiple ways. The results can be represented in an object-oriented format in which multiple associated pixels are replaced by an object representing those pixels in each of the different layers. For each of the layers, there are different local values associated with a coregistered object. In the Definiens Cognition Network Language (CNL), a Definiens proprietary scripting language for implementing data analysis transforms the image layers into the local values associated with the image objects. The local values can also be transformed vice versa back into the image layers. The objects could have a size even down to the size of a single pixel. As both representations are equivalent, we concentrate here only on the description of layers. Below, the storage of feature vectors into local values is discussed. In another representation, the statistical analysis results for each tile and each feature vector are stored in a table or database together with the associated x-y location of the tile from which the feature vector was created. This table can be transformed into layer values or local values in the hyperspectral image. Thus, the hyperspectral image can be created using the values in the table because the locations of the pixels and of the corresponding hyperspectral layers are defined within the table.

The tiles are coregistered either because the slices were coregistered beforehand or a transformation formula has been worked out that is applied to define in which position and with what rotation angle and scale the tiles are cut from the full slices. The n different slices are assessed by analyzing all the tiles taken from the slices. The analysis of different tiles can be performed in parallel on many computing nodes, thus enabling an efficient way to speed up the processing. Rich minable data is retrieved by detecting and classifying objects within the tiles at high resolution. Object properties of certain object classes and properties of relations between image objects of certain classes are calculated and stored in tables, local values of objects, or in the form of layer values in image layers.

The transformation of the local values associated with the image objects into the image layers generates a hyperspectral image by co-analysis of the coregistered image slices. A final image analysis is then executed on the small hyperspectral image (heat map). This final image analysis is performed following the same principles as applied for the image analysis of the digital images of the tissue slices. Preferably the analysis is performed using the Cognition Network Technology (CNT) of Definiens AG to extract very rich information. Pixels or tiles with similar feature vectors or layer values are combined into objects. Objects that conform to class descriptions are classified through context and knowledge driven image analysis. Hierarchical objects are also created. As a final comprehensive result, the object and hierarchical relation properties of the image objects are measured, exported and stored in a storage medium in the form of feature vectors. This final feature vector represents a tissue-based fingerprint of the health state of the patient that is much more advanced, sophisticated and valuable than the sum of all image analysis results of the different slices. This type of analysis allows the heterogeneity of tissue to be evaluated, in particular the heterogeneity of tumors. This heterogeneity can be investigated with a high precision in a simple manner because the local hyperspectral information is represented in a compressed form suited for normal advanced image processing.

The hyperspectral images generated by co-analysis of coregistered image slices can be used in the field of digital pathology. In digital pathology, digital images of tissue slices that have the required high spectral resolution have huge image sizes of several Giga-pixels. Because sophisticated image analysis tasks can be performed only on a limited amount of data at one time, efficient data handling is essential. While basic pixel processing can be performed on images of complete slices at low resolution, more complex image analysis functions are no longer employed on images at a high resolution that a pathologist could visually evaluate. In order to analyze a high resolution image, either the complex analysis functions are performed only on low-resolution sampled portions of the image, or the high resolution image is subdivided into regions (here called tiles) and each region is processed separately. The novel method of performing correlated analysis of coregistered images combines both approaches.

The method makes information available in a low-resolution multispectral version of the analyzed image that would otherwise be available only in a high resolution image. In the context of digital pathology, "high resolution" means that sub-compartments of cells are clearly visible in the images of the slices. The method allows for the collection of information from several related images (coregistered tiles) and for the parallel processing of the tiles.

The method analyzes a set of high-resolution images of consecutive, adjacent tissue slices from a patient that are obtained from differently stained tissue slices cut from the same tissue sample. Additionally, a coordinate transformation is performed that converts corresponding positions from each slice to the coordinates of the other slices. In a first embodiment, an affine transformation is used that is derived from the positions of three corresponding landmarks in each slice. The landmarks are set manually. Given a set of three points P1A, P2A and P3A in an image A and three points P1B, P2B and P3B in an image B, the transformation exactly maps P1A on P1B, P2A on P2B and P3A on P3B. All remaining positions on the slices are interpolated linearly. Thus, the method performs a registration by translation, scaling and rotation into one common coordinate system, e.g., the coordinate system of image A. In other embodiments, coregistration approaches can be used that include automated landmark detection and non-linear transformations, e.g., with splines. These approaches optimize the coregistration to find a best fitting overlay of corresponding images.

In the first embodiment, one slice is assigned to be the master image from which a downscaled small image is derived. The small image is then subdivided into tile regions. Each small image is prepared to store hyperspectral data. For all coregistered slices, the shape of the tiles is the same, and there is a spatial isomorphism between the tiles. Different tile shapes can be used for different image analysis projects, but in most cases the tiles are simply squares. The projected shapes of the tiles are then used to capture and produce high resolution tiles from the master image by copying raster data contents to sub-scenes according to the coordinate transformation. The resulting high-resolution sub-scenes can then be analyzed in parallel. Because all tiles are tagged with a tile ID and emerging coregistered sub-scenes for each stained slice carry corresponding tile IDs, it is possible to track, collect and interchange information between the tiles.

FIG. 1 illustrates the production and processing of the high-resolution sub-scenes (tiles) from a master image. FIG. 1 shows a high-resolution master image 20 of a tissue slice 21 from which a downscaled image 22 copy is made. Downscaled image 22 is a small image formatted in a manner capable of storing hyperspectral data. For each tile object of the downscaled image 22, information obtained from the corresponding full-resolution tile is stored. The tile objects of the gridded downscaled image 23 are projected onto the full resolution image 20 and define shapes of the tiles 24. In preprocessing steps, the full resolution tiles are processed in parallel to perform image analysis. Finally, FIG. 1 illustrates the transfer in post-processing steps of image analysis results back to the tile objects linked to image 23.

Figure 2:
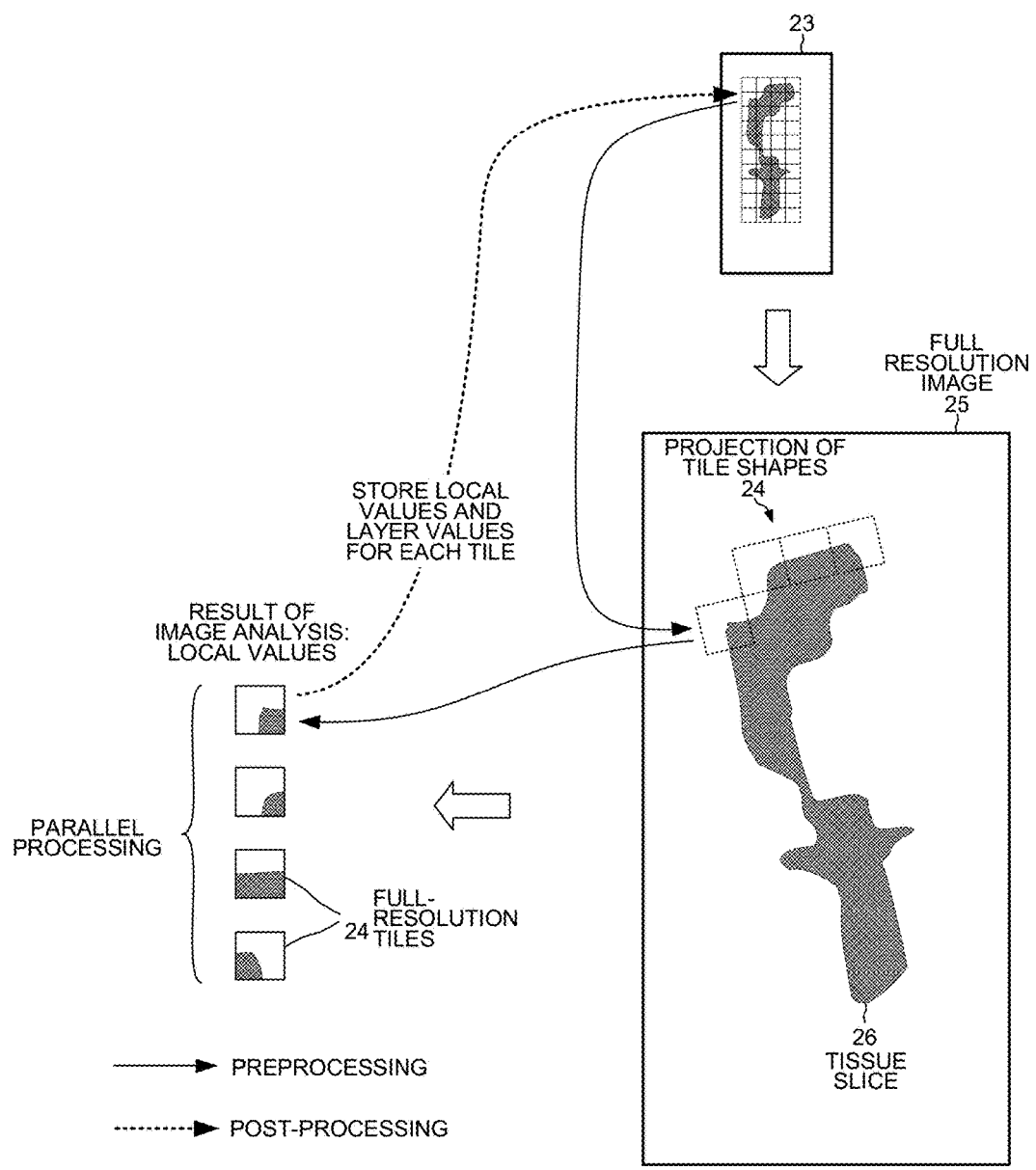
FIG. 2 is a diagram illustrating coordinate transformation for coregistration of a second image slice stained with a different biomarker.

FIG. 2 illustrates how coordinate transformation for coregistration is performed in order to project tile shapes onto a second digital image 25 of another slice 26 of the tissue sample that has been stained with a different biomarker. FIG. 2 illustrates the same process as performed in FIG. 1 except that the tile shapes are projected onto the other slice 26 with the different stain. When retrieved from staining, the other slice 26 is not aligned with first slice 21. Because coregistration of full-resolution images can consume a large amount of memory and processing resources, it is more efficient to perform the transformation and coregistration on a tile-by-tile basis. Each tile of the differently stained second slice 26 is then matches to its corresponding master tile, and image analysis results are transferred to corresponding tile objects generated with the gridded downscaled image 23 from the master image.

Figure 3C:
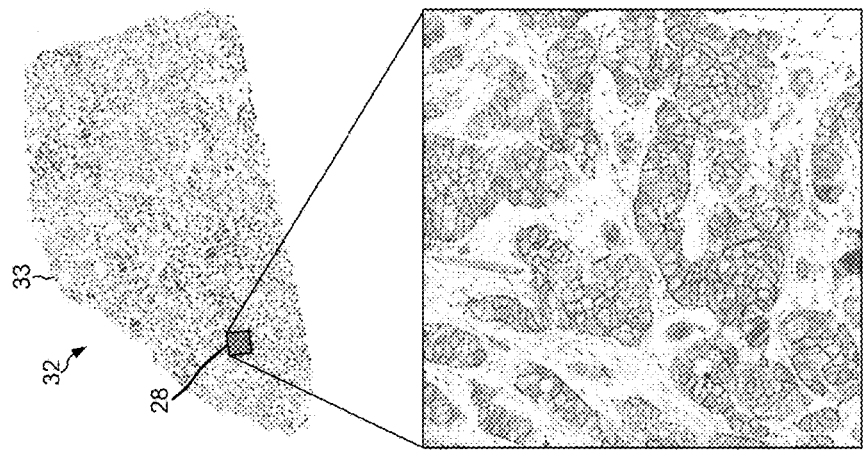
FIGS. 3A-C show the corresponding positions and coregistered contents of three differently stained slices of a sample tissue, including a sample position of a single tile.
Figure 3B:
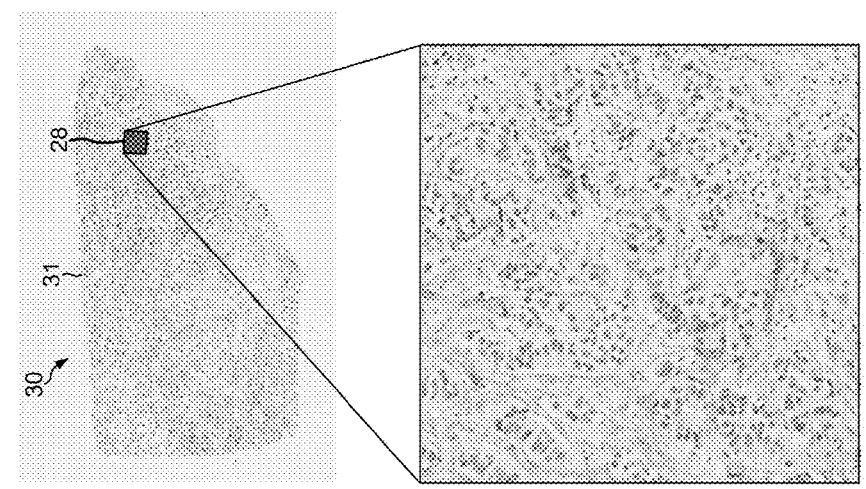
Figure 3A:
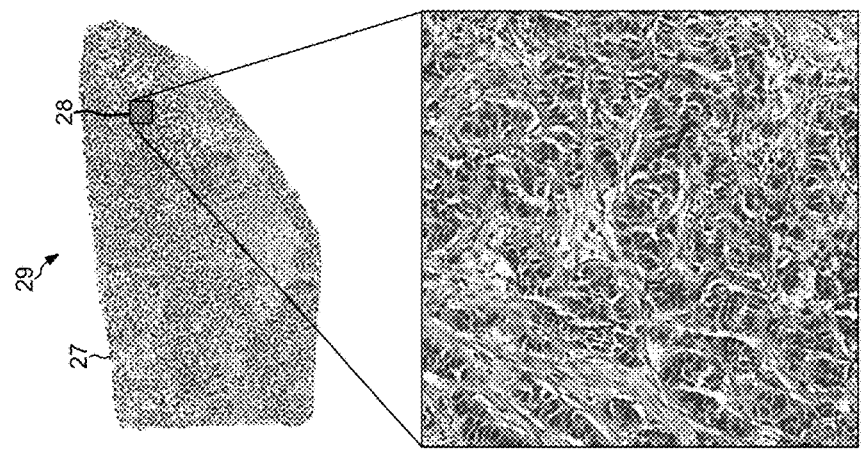

FIGS. 3A-C show the corresponding positions and coregistered contents of three differently stained slices of a sample tissue. FIG. 3A shows a slice 27 assigned to be the master and a sample position of a single tile 28 on a downscaled image 29. FIG. 3A also shows tile 28 in high resolution. FIG. 3B shows a downscaled image 30 of another slice 31 upon which the shape of tile 28 is projected. Slice 31 of the tissue is stained with a different biomarker than is first slice 27. FIG. 3B also shows a high resolution image of tile 28 obtained from the high resolution image from which second downscaled image 30 was generated. FIG. 3C shows a downscaled image 32 with the shape of tile 28 (determined from the master image in FIG. 3A) projected on a slice 33 in which the tissue has been rotated about 180° compared to FIG. 3A. The slice in FIG. 3C has been stained by yet another biomarker. FIG. 3C shows the high resolution image of tile 28 obtained from the high resolution image from which third downscaled image 32 was generated.

Figure 4:
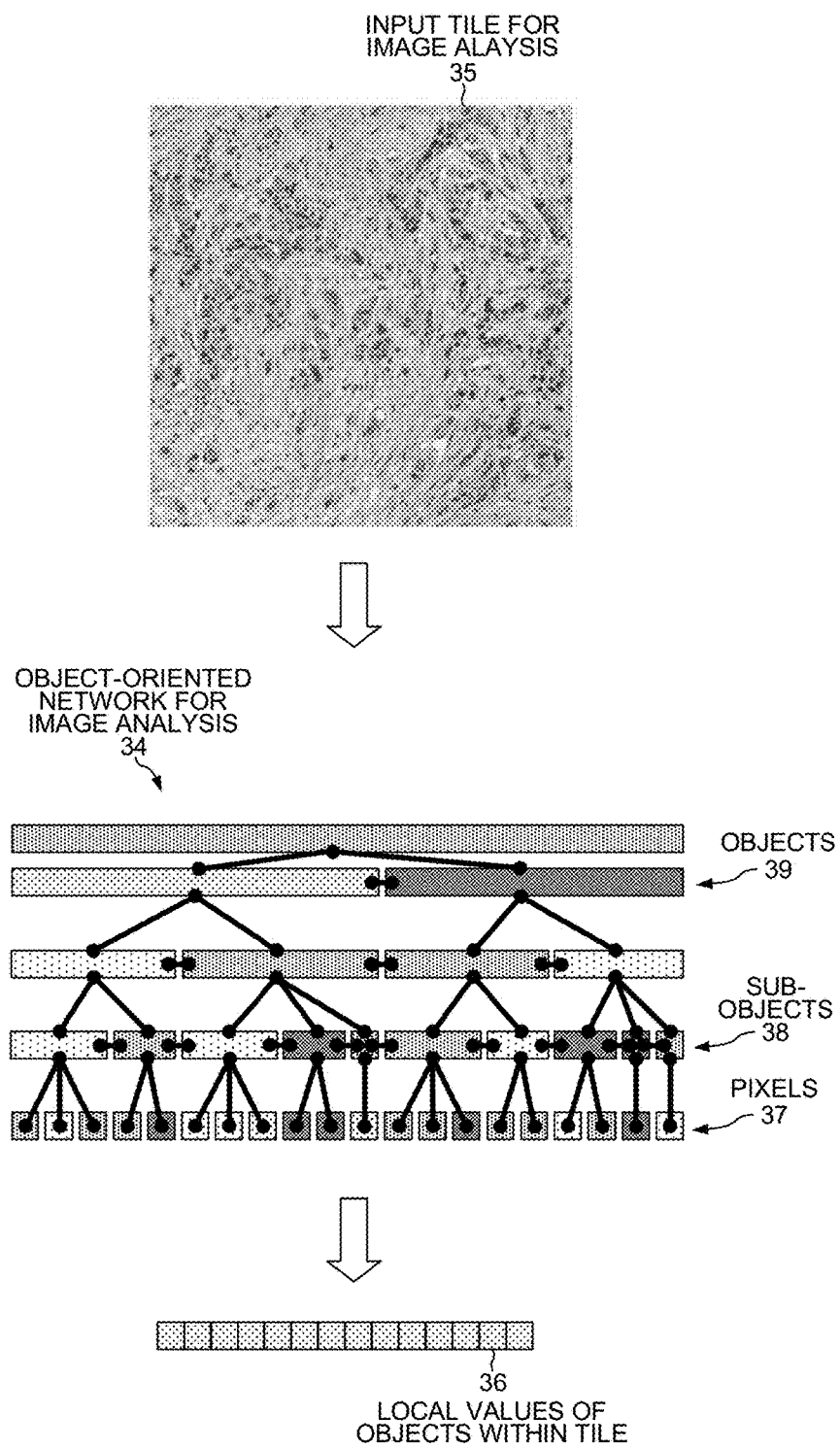
FIG. 4 illustrates an object-oriented cognition network and an output vector generated from a high-resolution tile of an image slice.

FIG. 4 illustrates the image analysis performed on the high resolution tiles. An object-oriented cognition network 34 is generated from a high-resolution input tile 35 upon which image analysis is performed. The object-oriented network 34 is used to generate an output vector 36 made up of the local values of objects within tile 35 that are defined by the network 34. Pixels 37 are linked together to form sub-objects 38. Sub-objects are classified as belonging to objects 39. For example, an object could be a cell, and one local value could be the diameter of the cell. The values quantifying many characteristics of the cell together make up the output vector 36. Thus, the image analysis operates on tiles and produces vectors with local values. All feature vectors from all tiles from all the coregistered slices are stored in layers of the formatted downscaled image 23. This means for an equal number of features for the different slices, n*N layers will be produced. In most cases this leads to a large number of layers representing a high level of complexity that is, however, compensated by the small image size of the hyperspectral downscaled image 22. Alternatively, resulting data is stored as variable values of corresponding tile objects or together with spatial information in a database for storage and further processing.

Figure 5:
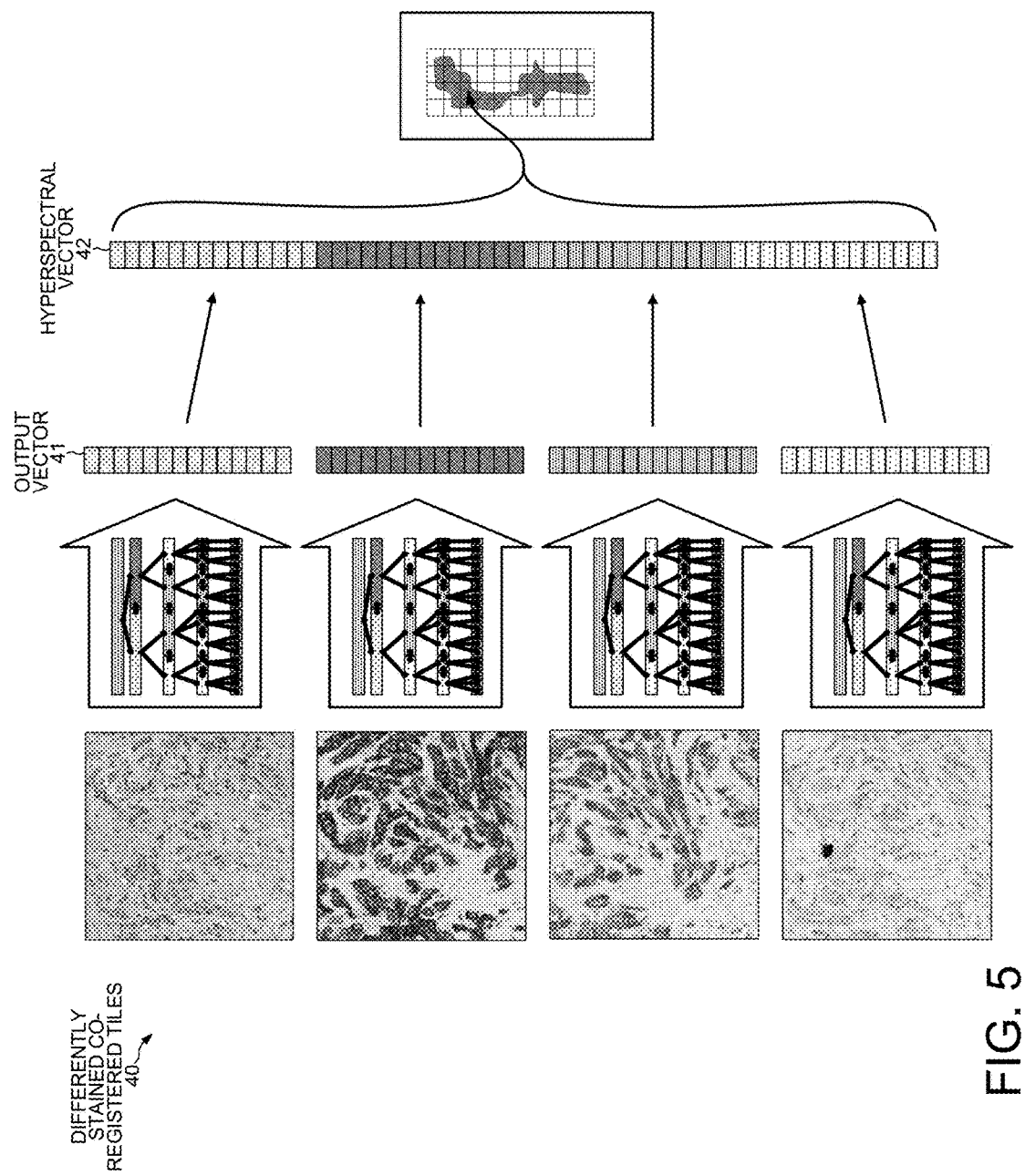
FIG. 5 illustrates a tile with a combined feature vector being generated from the coregistered positions in differently stained tissue slices.

FIG. 5 shows how the processing of a tile from corresponding positions in differently stained slices results in a combined feature vector, which then is linked to its tile region or object. Image analysis is performed by Cognition Network Technology (CNT) software on each of the differently stained coregistered tiles 40 to produce an output vector 41. The output vectors 41 for the various slices are then combined into a hyperspectral vector 42. Each hyperspectral vector 42 is then assigned to the corresponding tile object of formatted downscaled image 23. The image analysis performed by the CNT software is customized for each stain such that the output vectors 41 carry specific stain-related information.

Figure 6:
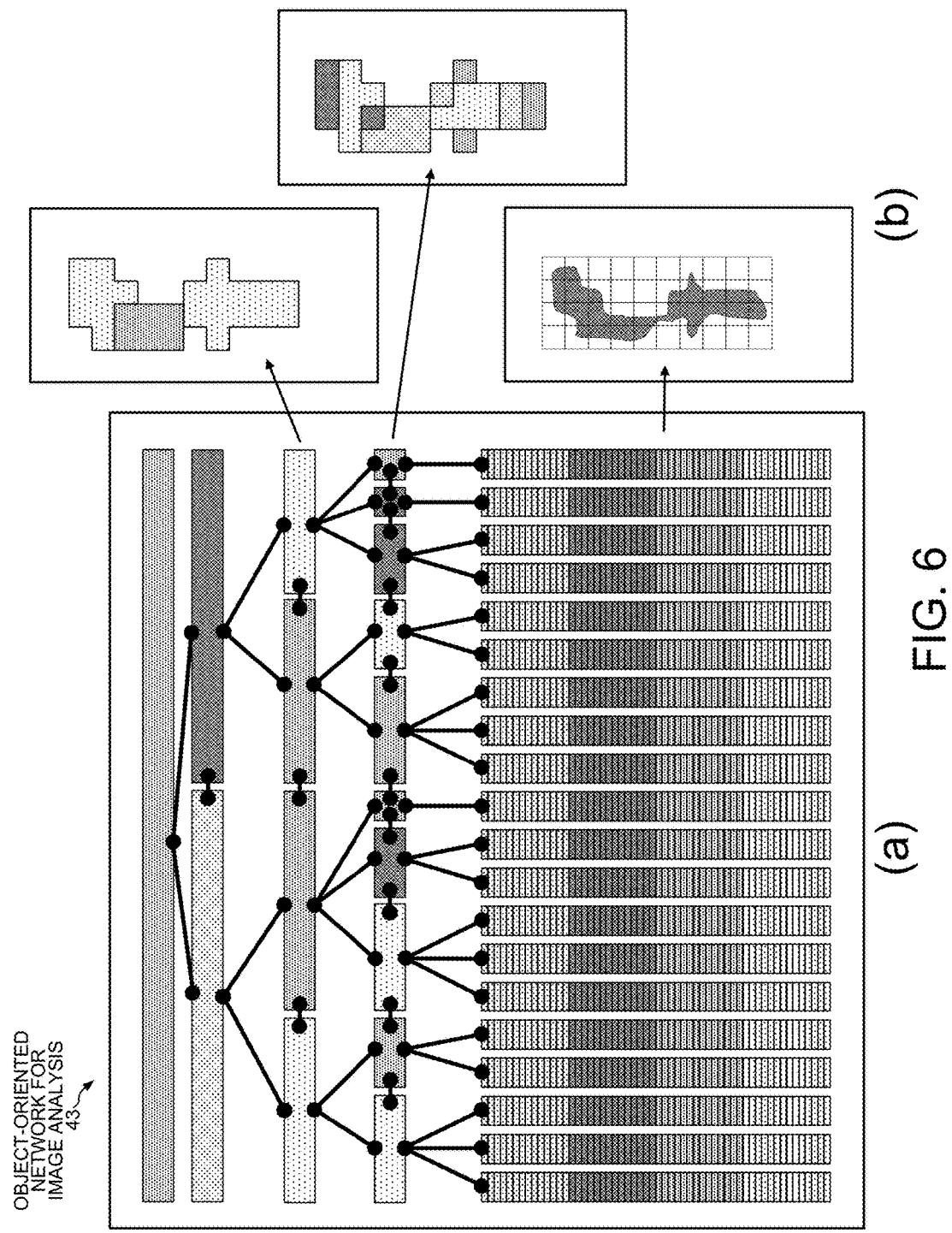
FIG. 6 is a diagram of an object-oriented network generated using tile information and feature vectors from differently stained tissue slices.

These steps are performed for all tiles. The resulting vectors with features from different stains constitute the basis for a new object-oriented Cognition Network 43, as shown in FIG. 6. FIG. 6(a) shows a Cognition Network based on vectors with tile information from the image processing of FIG. 5. This hyperspectral data is stored in a database as objects of the layers of network 43. FIG. 6(b) shows an analysis solution obtained by creating CNT objects of higher order. Each object in a hierarchical layer of network 43 is linked to one or more objects in a lower hierarchical layer. The lowest layer is no longer data related to individual pixels but rather multispectral data associated with a lower resolution tile that has been stained by multiple biomarkers. Because the input information originates from spatially ordered tiles, the information can be formatted and displayed as a multispectral image or heat map with the resolution of the tiles. In this sense it is a coarse representation of the master slice carrying information from high resolution processing of coregistered tiles with different stains. Using this procedure, it is possible to continue and create solutions with CNT like in traditional processing with single images.

Figure 7:
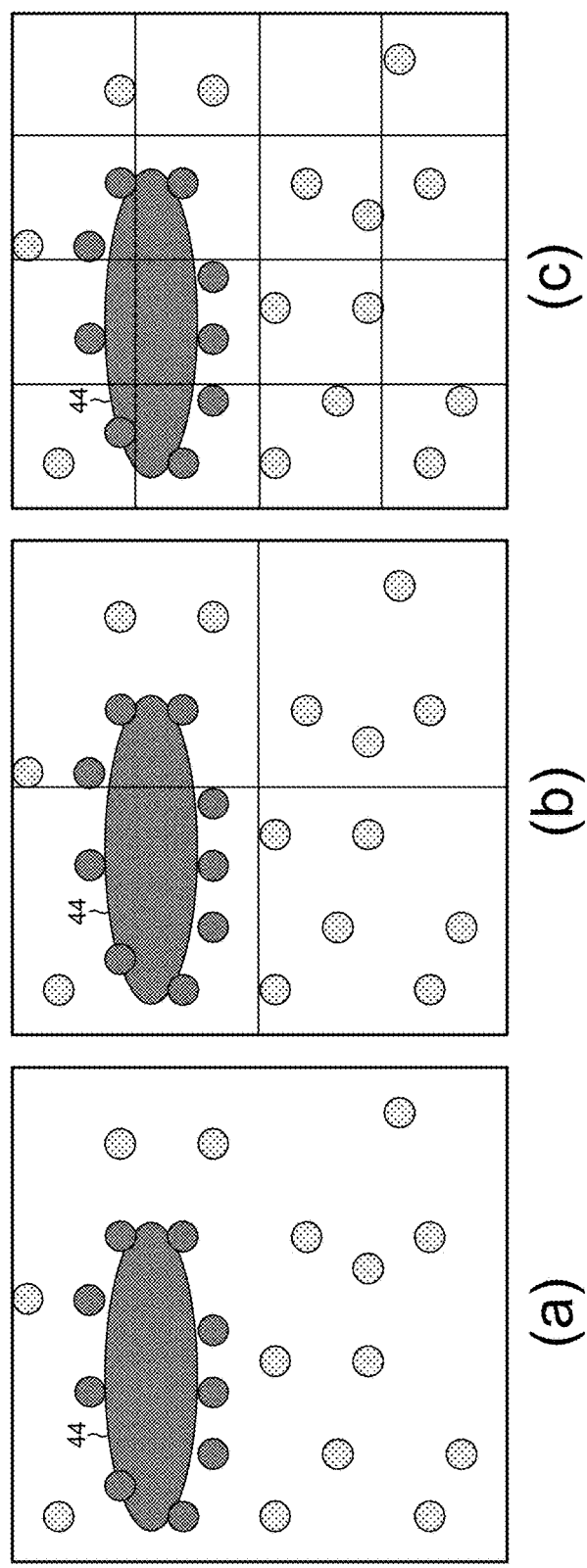
FIG. 7 shows a physical object of a tissue slice split between different neighboring tiles of an image of the slice.

The CNT software also enables local virtual processing involving virtual stitching, virtual fusion and virtual objects. When applying the method described above, very often objects at the boundaries of the tiles are cut in two or more pieces that belong to different neighboring tiles. The CNT software stitches the pieces together into one object at a higher level of the object-oriented network. Thus, multiple sub-objects of the network can belong to an upper object that represents a physical object, such as the same lumen, membrane or nucleus. For nuclei, the problem of splitting physical objects at the boundaries of tiles is of less importance as there are usually many more nuclei within the tile than those located at the border of the tile. As for the method described here, the statistical evaluations represent the key values, and any errors produced by small objects lying at the tile borders are relatively small. This is not the case for bigger objects such as lumina. The uncertainty of the classification of bigger objects located at the tile boundary must therefore be resolved. The CNT software determines how correctly to classify and how to assign the parts of the "whole" original physical object to each other in the object-oriented networks. The pieces representing parts of the same physical object are contained in more than one of the neighboring tiles as shown in FIG. 7. The relatively large object 44, which could represent a lumen, is separated into two or more pieces, which are contained in separate tiles. FIG. 7(b) shows object 44 separated between two tiles, and FIG. 7(c) shows object 44 separated between six tiles.

As a solution to the problem of physical objects being split at the boundaries of tiles, objects that lie at a tile border are classified as "potential objects" (for instance "potential lumen") while a single tile is being analyzed and before the full structure is detected. After segmentation and classification of all tiles, there are some objects classified as "potential" lumen objects at the boundaries of the tiles. Stitching all high-resolution tiles into one big image would result into too much data to be analyzed. Stitching together low-resolution tiles would result in imprecise stitched objects. Therefore, a small group of high-resolution tiles are stitched together at one time. Which groups of tiles are stitched together is defined by specific decision criteria generated by the CNT software.

Such decision criteria are based on whether a given "potential object" abuts one of the selected borders. The selected borders define the groups of tiles that will be virtually merged as each selected border connects two tiles. The terms "virtual merge" and "virtual stitching" mean that the tiles are combined into a bigger region only for the purpose of performing final segmentation and classification of the potential objects. After this final classification of the potential objects is performed, the region is cut again into the previous tiles, and the statistical values for the individual tiles are calculated and stored.

In order to select the members of the groups of tiles to be stitched, each tile is investigated to determine whether its potential objects could belong to a whole object. If a tile is found that has potential objects attached to its borders, it is selected as a "starting tile." One possibility for selecting the other members of the group to be stitched is that all existing "selected borders" of one tile are picked to define the "neighboring tiles" as members of the group. Another possibility is that only one potential object in the starting tile is picked, and only those borders are defined as selected borders that are connected to this particular potential object. In the second possibility, a particular tile might have to be used as a starting tile several times in contrast to the first possibility where it will only be used as a starting tile once.

Additional members of the groups of tiles to be stitched might have to be selected if the potential object in a neighboring tile that touches the selected border also touches other borders of the neighboring tile besides the selected one. In this case, those other borders are also defined as selected borders, and the corresponding neighbors become part of the group of tiles as well. In the case where relevant objects that are extended over a large number of tiles or even the whole slide, this method will not be successful. In tissue slices, however, this usually does not occur for most relevant individual objects.

However, groups of similar relevant objects do commonly extend over a large number of tiles. An inflammation or a cancer region could represent such a case. For such large super-structures, merging the super-structures within many tiles can be managed using down-scaled tiles where the density of cancer nuclei or of inflammation nuclei is represented as layer values. When stitching all members of a particular group into one region, the members are positioned relative to each other in a way that corresponds to their neighborhood position in the original slice. This way an individual tile might be part of several groups and therefore is potentially treated several times. On the other hand, by this procedure the groups stay small and consist of at most nine tiles if potential objects in the neighboring tiles do not extend over more than one border line.

The CNT software performs several steps in order to detect objects of interest in multiple coregistered slices. The following lists the steps for detecting a lumen. First, objects in each tile are segmented and classified. Objects at the boundaries of the tiles are classified as "potential" lumen objects. Tiles containing potential lumina serve as starting tiles. Borders in the starting tiles with abutting lumina objects are defined as "selected borders." Each starting tile is stitched together with several other neighboring tiles into one region. Only those neighboring tiles are selected that are connected to a selected border of the starting tile. Neighboring tiles that are positioned diagonal to the starting tile are selected as well when they are connected to a selected neighboring tile. After a tile is stitched with its appropriate neighbors into a region, the potential lumina objects within the region are segmented and classified. Objects in the starting tile are measured, and statistical data from the objects in the starting tile are calculated and stored.

For image analysis and related feature generation, it is beneficial to work on tiles that are not too small. Tiles should not be so small that most of the objects of interest do not fall entirely within one tile. In addition, smaller tiles lead to a larger number of tiles. Performance is improved by reducing data-handling overhead if the number of tiles is reduced. On the other hand, local multispectral resolution is limited by tile size. To solve this contradiction, sub-tiles are introduced. Image processing is performed on tiles having the predetermined size required for proper feature generation, and then these tiles are subdivided into sub-tiles. Because tiles are typically square, sub-tiles are also square. For each sub-tile, local statistics are calculated and stored for further processing. Then feature-vectors of these sub-tiles constitute the base elements for the built-up object-based network 43 shown in FIG. 6. The feature vectors provide a higher resolution compared to the image processing size of the tiles.

Figure 8:
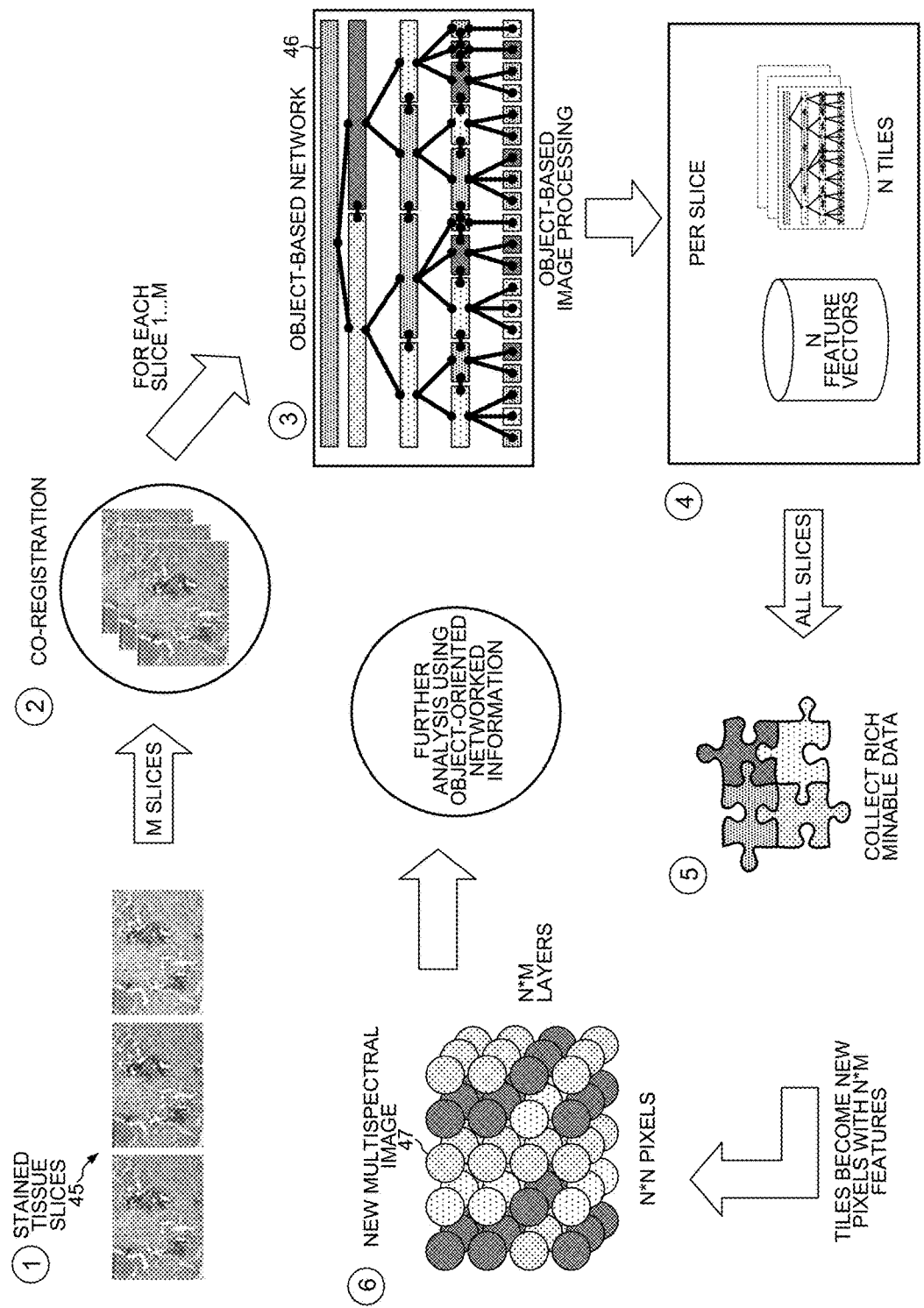
FIG. 8 is a diagram illustrating the steps for extracting information from hyperspectral images generated from coregistered tissue slices stained with different biomarkers.

FIG. 8 illustrates the steps of extracting information from hyperspectral images generated from coregistered tissue slices stained with different biomarkers. In step 1, multiple adjacent tissue slices 45 are stained with different biomarkers, for example, M slices. In step 2, digital images of the M slices are coregistered. For example, the digital images are digital pathology slides. In step 3, the digital image of each of the slices is analyzed using an object-based network 46. In step 4, each slice is divided into N tiles. Each of the N tiles is processed separately. A feature vector is generated for each of the N tiles. In step 5, information from coregistered tiles is correlated with each other. Due to coregistration, each tile of one slice is linked to comparable tiles of differently stained slices. After collecting the data from all slices, the resulting data is formatted as a new multispectral image 47 in step 6. Each tile and its corresponding feature vector is associated with a pixel of the multispectral image (heat map). The tile becomes a pixel, and the corresponding feature vectors (concatenated from all stains) are layers of information linked to the pixel. Thus, the new multispectral image is structured as an object-based network such as network 43 of FIG. 6. Further image analysis is performed on new image 47.

Figure 9:
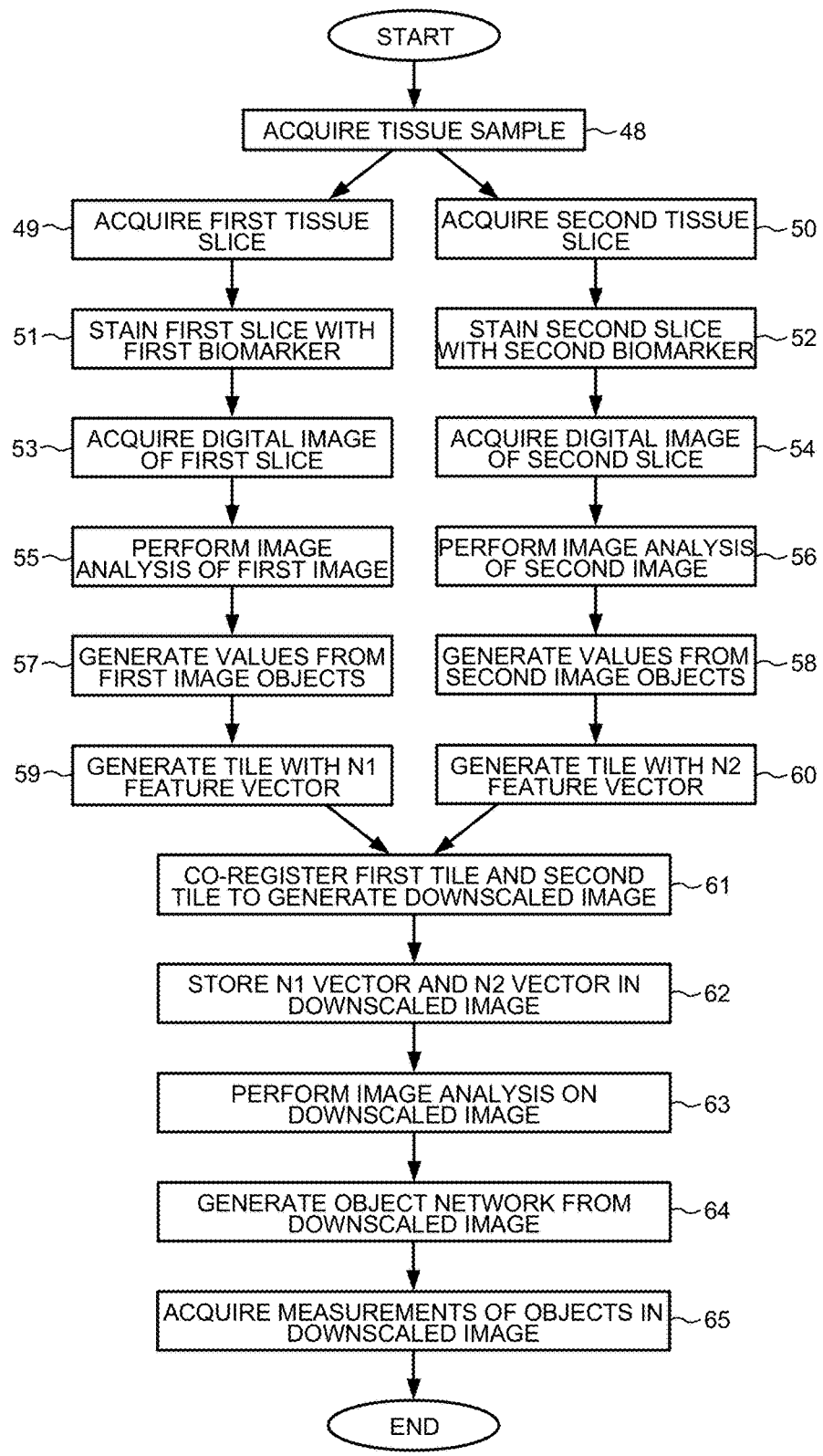
FIG. 9 is a flowchart of steps for extracting information from hyperspectral images generated from coregistered tissue slices stained with different biomarkers.

FIG. 9 illustrates a more detailed embodiment for extracting information from hyperspectral images generated from coregistered tissue slices stained with different biomarkers. In a first step 48, a tissue sample is obtained from a patient. In steps 49-50, the tissue sample is sectioned and transferred to glass slides. A section identifier (SID) is associated with each section (slice). Several slices are taken in consecutive order, and that order is stored with the section SID. In steps 51-52, the tissue on each glass slide is processed with a predefined protocol and method. For example, the first slice is stained with a first biomarker in step 51, and the second slice is stained with a different biomarker in step 52. Common staining methods used in histology are H&E staining, immunohistochemistry (IHC) and immunofluorescence (IF). In steps 53-54, each slice is digitized using a digital microscope or a tissue slide scanner, and the resulting digital image is stored in a database.

In steps 55-56, the CNT software uses image analysis algorithms or rule sets to processes the image of each slide (slice). The algorithm depends on the type of staining applied to the slice of tissue. The image analysis algorithm detects large, medium, small and fine scale image objects in each image. The objects are defined as elements of a hierarchical object-oriented network. In steps 57-58, values and numerical data are generated from the objects of the network using another rule set. For example, one value is obtained from cell objects and corresponds to the number of mitotic objects in a defined area of an H&E stained tissue slice. Another value corresponds to an Allred score measured on an immunohistochemically stained tissue slice. In steps 59-60, the image of each slice is divided into tiles. A set of statistical image object features in the form of numerical data is calculated for each tile. The image object features are linked as a feature vector to the corresponding tile. Other examples for values and numerical data obtained from cell objects are (i) the number of T, B, M1 or M2 cells within a predefined distance to tumor cells, and (ii) the number of tumor cells stained positive with a protein-specific antibody using immunohistochemistry. Cells are considered to be stained positive when their cell compartments, such as the membrane or nucleus, are stained more intensely than a threshold.

In step 61, a downscaled image is generated using the tiles of the images of the slices. Corresponding tiles of adjacent slice images are coregistered. Each tile becomes a pixel of the new downscaled hyperspectral image. The multiple coregistered tiles of the various slices make up multiple image channels of the downscaled hyperspectral image. The value of a pixel in a single image channel corresponds to the feature value of one of the associated tiles. The name of the image channel is associated with the name of the extracted feature.

In step 62, the feature vectors of each of the multiple coregistered tiles are stored as part of the hyperspectral image or heat map. The feature vectors are linked to the associated pixel. In step 63, the hyperspectral image is displayed on a computer monitor, or an additional image analysis process segments the hyperspectral image, measures the generated image objects and stores those objects on a computer file system. In step 64, a hierarchical object network is generated from the objects obtained from image analysis performed on the new downscaled hyperspectral image. In step 65, statistical values and numerical data are obtained by measuring the network objects in the downscaled hyperspectral image.

Hyperspectral images can also be coregistered with each other. A hyperspectral image obtained from several tissue slices is registered to another hyperspectral image obtained from adjacent tissue slices. The registration utilizes those image channels (stains) that show the best correlations across the slices. By registering multiple hyperspectral images with each other, yet another hyperspectral image is generated that combines the channel values from all tiles of all tissue slices.

FIG. 9 depicts the steps performed to obtain measurements from hyperspectral images generated from tissue slices stained with multiple biomarkers. The procedure is used to diagnose the state of a patient using a multiplexed tissue-based test. H&E staining may be multiplexed with IHC markers, or several IHC markers may be used in tissue processing, or H&E, IHC and IF may be used altogether. One specific application is a breast panel in which H&E, IHC ER, PR and HER2, and IF HER2 and Chr17 are used. By creating a hyperspectral image from consecutive sections of a tissue sample, the novel method allows the generation of hyperspectral image objects that provide a rich descriptor set. In diagnostics development, this descriptor set can be correlated with clinical endpoints. One application may use a fuzzy classifier to predict the disease free survival time using the properties of image objects generated from the hyperspectral image. Using a false-color visualization of the hyperspectral image, it is possible to depict the specific subtype of a tumor present in the tissue sample, or to discriminate between various types of inflammation cells according to their spectral profile.

Figure 10:
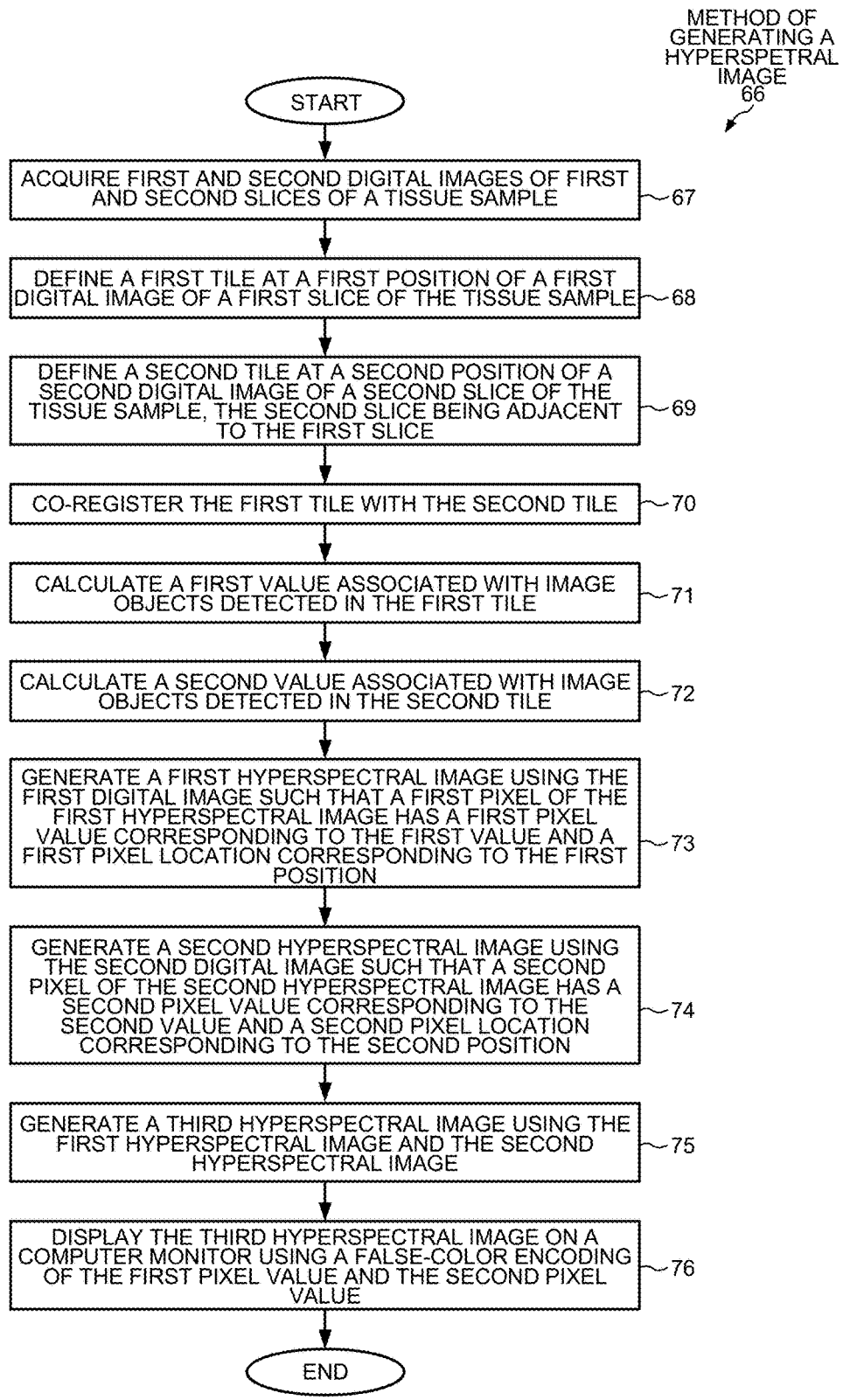
FIG. 10 is a flowchart of another embodiment of a method for analyzing digital images to generate hyperspectral images.

FIG. 10 is a flowchart of another embodiment of a method 66 for analyzing digital images to generate hyperspectral images. In method 66, tiles of the digital images are coregistered instead of the entire full-resolution images themselves. Method 66 includes steps 67-76 in which multiple hyperspectral images are combined to generate a hybrid hyperspectral image that provides diagnostic insights not otherwise retrievable from the digital images of tissue slices. In one implementation, the various tissue slices are each stained with a different biomarker.

Figure 11:
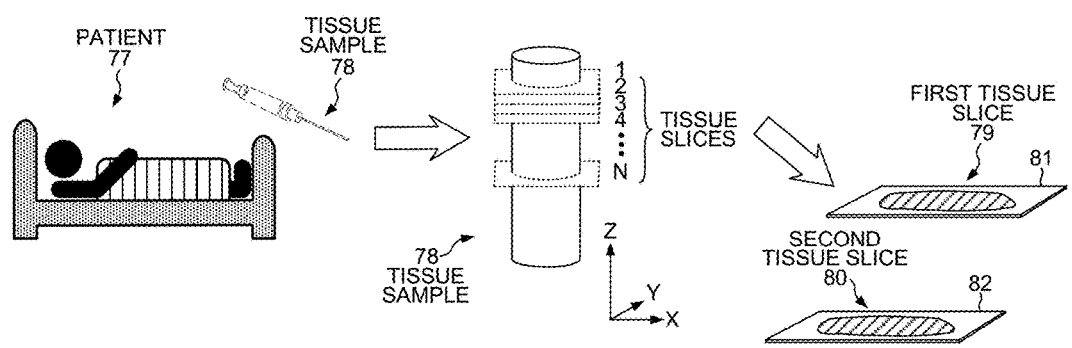
FIG. 11 is a diagram illustrating the process of acquiring the digital images whose tiles are to be coregistered and used to generate hyperspectral images.

In a first step 67, digital images are acquired from slices of a tissue sample. FIG. 11 illustrates the process of acquiring the digital images that are to be used to generate hyperspectral images and whose tiles are coregistered. The tissue portions that are to be stained with various protein and receptor biomarkers are typically taken from a live patient 77 in the form of a biopsy. The tissue sample 78 is then sliced into many slices. The planar slices are adjacent to one another and are located at the same position of the tissue sample in the x and y dimensions. FIG. 11 shows a first slice 79 on a first slide 81 as well as a second slice 80 on a second slide 82. Second slice 80 originated from tissue sample 78 adjacent to first slice 79.

Before being put on a slide 81, first slice 79 is stained with a first biomarker. In some implementations, the slice is first placed on the slide and then stained with a drop of solution containing the biomarker. Second slice 80 is stained with a different biomarker. There are so many available protein and receptor biomarkers that it is a challenge meaningfully to apply the information of how each different biomarker stain reacts with a tissue sample. In one embodiment, the method combines the results of a limited number of well known biomarkers, such as hematoxylin and eosin (HE), Human Epidermal growth factor Receptor 2 (Her2) membrane stain, cytokeratin 18 (CK18) cytoplasmic stain, estrogen receptor (ER) stain, progesterone receptor (PR) stain, cell proliferation marker Ki67, basal cell marker p63, Mib, SishChr17, SishHer2, or cluster of differentiation (CD) 3, 8, 23 or 44 stains. For example, first slice 79 is stained with the Mib biomarker, and second slice 81 is stained with the cell proliferation marker Ki67. High resolution digital images are then taken of each stained slice. A first digital image 83 is taken of first slice 79, and a second digital image 84 is taken of second slice 80. In the field of pathology, the image is sometimes referred to as a "sectional digital image." In the field of radiology, the image is sometimes referred to as the "slice."

Because the slices are very thin, each slice contains practically the same types of tissue. The same tissue reacts uniquely with each different biomarker. So the most meaningful information can be obtained by comparing how the same particular tissue was stained by multiple different biomarkers. In order to determine which locations on different slices correspond to the same tissues, however, locations on the two digital images 83-84 of slices 79-80 must first be coregistered with one another. When each slice is removed from the staining solution, the slice may be in any orientation, for example, rotated about its center of gravity or flipped from its back side to front side. The higher resolution images 83-84 are acquired of the slices 79-80 in whatever orientation those slices are placed on the slides 81-82 after being pulled from the staining solution. In step 67, first and second digital images 83-84 are acquired of first and second slices 79-80 of tissue sample 78.

Figure 12:
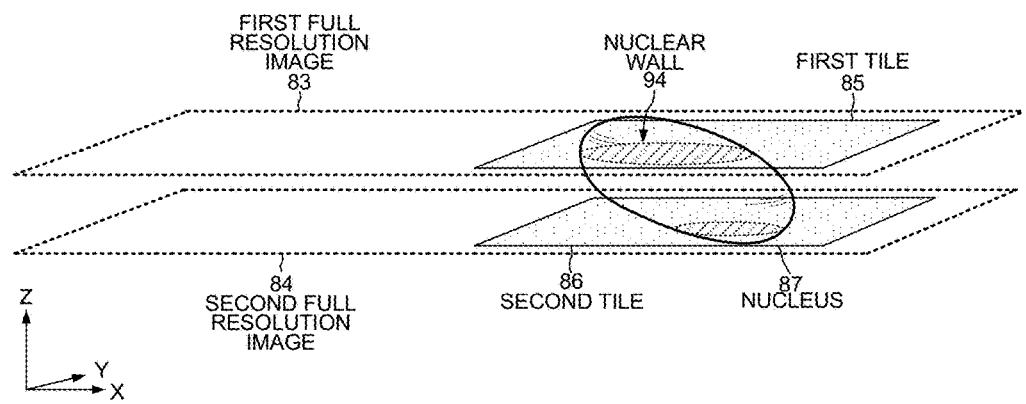
FIG. 12 is a diagram showing a first tile on a first digital image that is to be coregistered with a second tile on a second digital image.

FIG. 12 illustrates step 68 in which the CNT software defines a first tile 85 on first digital image 83 of first slice 79 of tissue sample 78. The dashed plane in FIG. 12 represents only a small portion of first full resolution digital image 83. Thus, first tile 85 covers only a small portion of the entire high-resolution image 83. First tile 85 is located at a first position in the x and y dimensions of first image 83.

In step 69, a second tile 86 is defined on second full-resolution digital image 84 of second slice 80 of tissue sample 78. Second tile 86 has a second position in second digital image 84 in the x and y dimensions. Because second slice 80 originated from tissue sample 78 adjacent to first slice 79, portions of some tissue objects are present in both slices. For example, cross sections of portions of a nucleus 87 are present in both first image 83 and second image 84.

Figure 13:
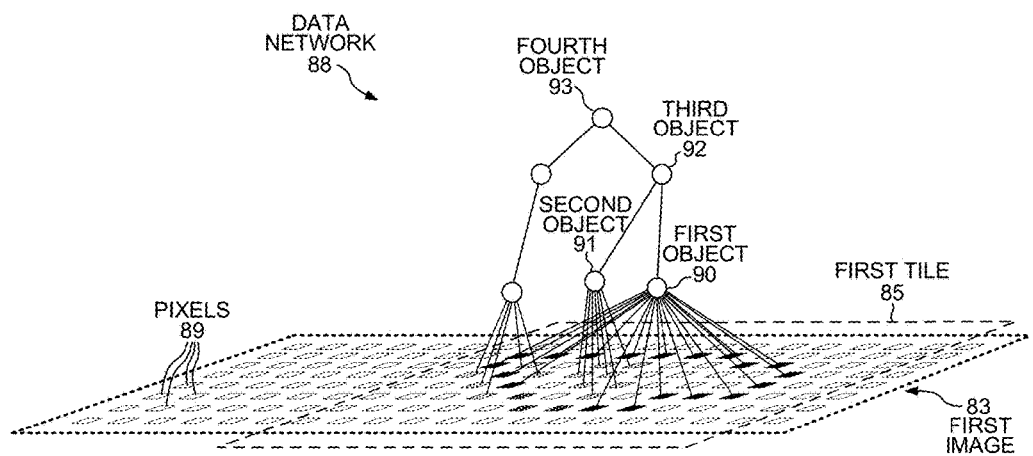
FIG. 13 is a diagram of a data network generated by performing image analysis on the first digital image of FIG. 12.

FIG. 12 is not drawn to scale. The size of an actual tile would encompass many nuclei and cells. Image analysis is performed on each of images 83-84, and a hierarchical data network of image objects is generated for each image. FIG. 13 shows an exemplary data network 88 generated from first image 83. The CNT software generates data network 88 by selectively linking pixels 89 from digital image 83 to objects according to a process hierarchy of steps and algorithms and according to a classification network. First image 83 is comprised of pixel values associated with the locations of each of the pixels 89. The CNT software operates on the digital pixel values and links the pixels to form objects. Each object is linked to a set of pixel locations based on the associated pixel values. For example, data network 88 includes a first object 90, a second object 91, a third object 92 and a fourth object 93. First object 90 and second object 91 are generated by linking to each object those pixels having similar characteristics, such as brightness as defined by the pixel value. Thresholds of brightness at pixel locations that are grouped together can be obtained from a histogram of the pixel values in the digital image. The image objects are then linked together into classes according to membership functions of the classes. The image objects in network 88 represent instances of classes in the classification network that are detected by the CNT software. Objects in a lower hierarchical level that belong together are linked to the same object in a higher hierarchical level. In this manner, for example, all of the components of a nucleus can be linked together to form one image object "nucleus." For example, object 93 in FIG. 13 represents nucleus 87 in FIG. 12.

In step 70, corresponding tiles on digital images 83-84 are coregistered with each other. Coregistering pairs of tiles is less computationally intensive than coregistering entire full-resolution images. Moreover, coregistering tiles is more accurate than coregistering entire images because of stretching and skewing of the tissue slices. Thus, even if one entire image is optimally rotated and translated with respect to a second entire image, corresponding tissues will align only locally around the center of rotation but will be offset from one another at locations distant from the center of rotation due to stretching and skewing. Thus, coregistering pairs of tiles provides a better alignment of the tissues. The image objects in network 88 are used to coregister first tile 85 with second tile 86.

Each of the objects in network 88 can also be measured using data network 88. The CNT software generates values and numerical data associated with the measurements. For example, the length of the nuclear wall 94 represented by object 90 is measured as the number of contiguous stained pixel locations that make up a one-pixel wide nuclear wall. By filtering out pixel values, an edge filter removes pixels from first object 90 that form a wall more than one pixel wide, thereby simplifying the measurement of the length of the nuclear wall of object 90 of data network 88.

In step 71, a first value associated with image objects detected in first tile 85 is calculated. For example, the first value is the number of stained nuclei in the area of first tile 85. As stated above, nucleus 87 is not illustrated to scale in FIG. 12. Typically, dozens or even hundreds of nuclei would be present in the area of a tile. A tile includes thousands or millions of pixels. For example, the first value might be fifty stained nuclei in first tile 85. The CNT software generates image objects from those nuclei that have been stained by the first biomarker. Because first tissue slice 79 was adjacent to second tissue slice 80 in sample 78, portions of most nuclei appear in both first image 83 and second image 84. The nuclei react differently, however, to the different biomarkers. Because first tile 85 is coregistered with second tile 86, portions of most of the fifty stained nuclei from first tile 85 would probably also be present in second tile 86. Portions of a nucleus are not present in both tiles where the last end slice of a nucleus is present in one of the tissue slices.

In step 72, a second value associated with image objects detected in second tile 86 is calculated. For example, the second value is the average proportion of each nuclear membrane that has been stained. The nuclei might on average have only 75% of their membranes stained by the second biomarker.

In another embodiment, the first and second values are more complex than just the number or size of objects generated from image analysis. For example, the first and second values can be histopathological scores associated with a particular biomarker or biomarker combination, such as an Allred score, a Gleason score, an Elston-Ellis score or a HercepTest score. The Allred score indicates the percentage of cells that have been stained to a certain intensity by the estrogen receptor (ER) antibody. The Gleason score is based on the architectural pattern of the glands of the tumor tissue. The Elston-Ellis score is determined by summing scores for three parameters: tubule formation, nuclear pleomorphism and mitosis per ten high-power fields (HPF) of 400×. The CNT software uses image analysis to determine the proportion of tubules, the similarity of nucleus sizes and the number of dividing cells per high power field of 400× magnification. The HercepTest represents the level of HER2 protein overexpresssion based on the degree of membrane staining. Complete membrane staining of some tumor cells results in a high score irrespective of the percentage of tumor cells that are stained. The CNT software determines whether each membrane object has the stain color around the entire membrane.

The first and second values can also be statistical values based on the measurement of objects generated from image analysis. For example, the first value can be the mean, median (2-quantile), minimum, maximum or standard deviation of a property of a subset of the image objects detected in first tile 85. One example of a subset of image objects are those cells whose membranes are completely stained by a particular biomarker. Another example of a statistical value is a weighted mean. For example, the first value is calculated using a distance weighted mean of a property of a subset of the image objects detected in the first tile, such as cells with stained membranes. The distance weighted mean is based on distances from the center of first tile 85 to the center of each of the stained cells.

Figure 14:
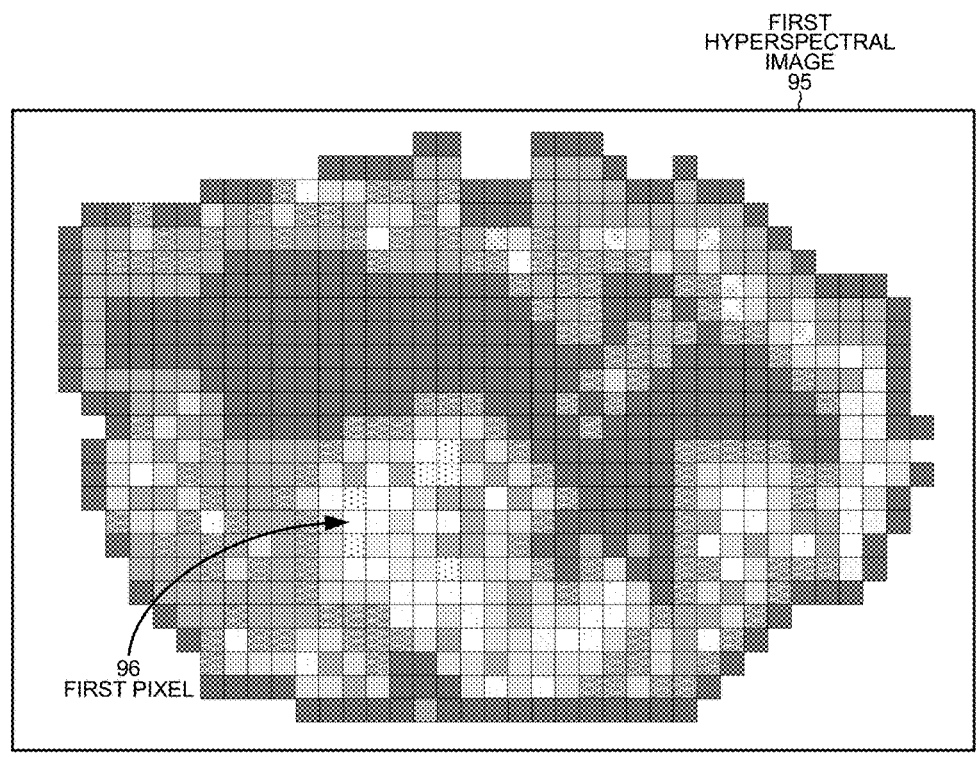
FIG. 14 is a hyperspectral image in which the location of each pixel corresponds to the position of a corresponding tile of the first digital image of FIG. 12.

In step 73, a first hyperspectral image 95 is generated using first digital image 83. Image 95 is a heat map. A first pixel 96 of first hyperspectral image 95 has a first pixel value corresponding to the first value and a first pixel location corresponding to the first position of first tile 85. FIG. 14 shows first hyperspectral image 95 in which the location of each pixel 96 corresponds to the position of the corresponding tile of first image 83. Thus, the location of first pixel 96 in first hyperspectral image 95 corresponds to the position of first tile 85 in first image 83. In the exemplary embodiment, the first pixel value corresponds to the number of stained nuclei in the area of first tile 85. In FIG. 14, a higher density of stained nuclei in first image 83 results in a brighter pixel in hyperspectral image 95. White first pixel 96 indicates that there are more stained nuclei in first tile 85 than in the surrounding tiles.

In step 74, a second hyperspectral image is generated using second digital image 84. A second pixel of the second hyperspectral image has a second pixel value corresponding to the second value and a second pixel location corresponding to the second position of second tile 86. Whereas brighter pixels in first hyperspectral image 95 indicate a higher density of stained nuclei, brighter pixels in the second hyperspectral image might indicate a higher malignancy of the stained cells. The malignancy is roughly proportional to the proportion of each nuclear membrane that is stained. Alternatively, brighter pixels in the second hyperspectral image could indicate the presence of a type of cancer that is more likely to respond to a particular type of drug, such as Herceptin® (trastuzumab).

In step 75, a third hyperspectral image is generated by combining first hyperspectral image 95 with the second hyperspectral image. For example, the third hyperspectral image provides a better indication of the tumor area in tissue sample 78. By combining the results of measurements performed on image objects detected in differently stained coregistered tissues, additional diagnostic information can be extracted from tissue sample 78.

In step 76, the third hyperspectral image is then displayed on a computer monitor using a false-color encoding of the first pixel value and the second pixel value. The combined results depicted in the first and second hyperspectral images are assigned colors based on ranges of numerical values of the results. In one embodiment, the first pixel value and the second pixel value are used to generate a false-color encoding using the hue, saturation and brightness color space. The hue component is calculated as the arctangent of the ratio of the first and second pixel values, the brightness is proportional to the sum of the first and second pixel values, and the saturation is constant. In another embodiment, the third hyperspectral image is generated by combining the first and second hyperspectral images with yet another hyperspectral image. The resulting three values for the corresponding pixels of the first and second hyperspectral images and the additional hyperspectral image are used to encode a false-color of red-green-blue (RGB) color coordinates. Each of the three values is mapped to one of the RGB color coordinates to define the color of each pixel of the third hyperspectral image displayed on the computer monitor. In addition to the combined results, it is also possible simultaneously to display the results of multiple hyperspectral images along with the combined hyperspectral image.

Figure 15:
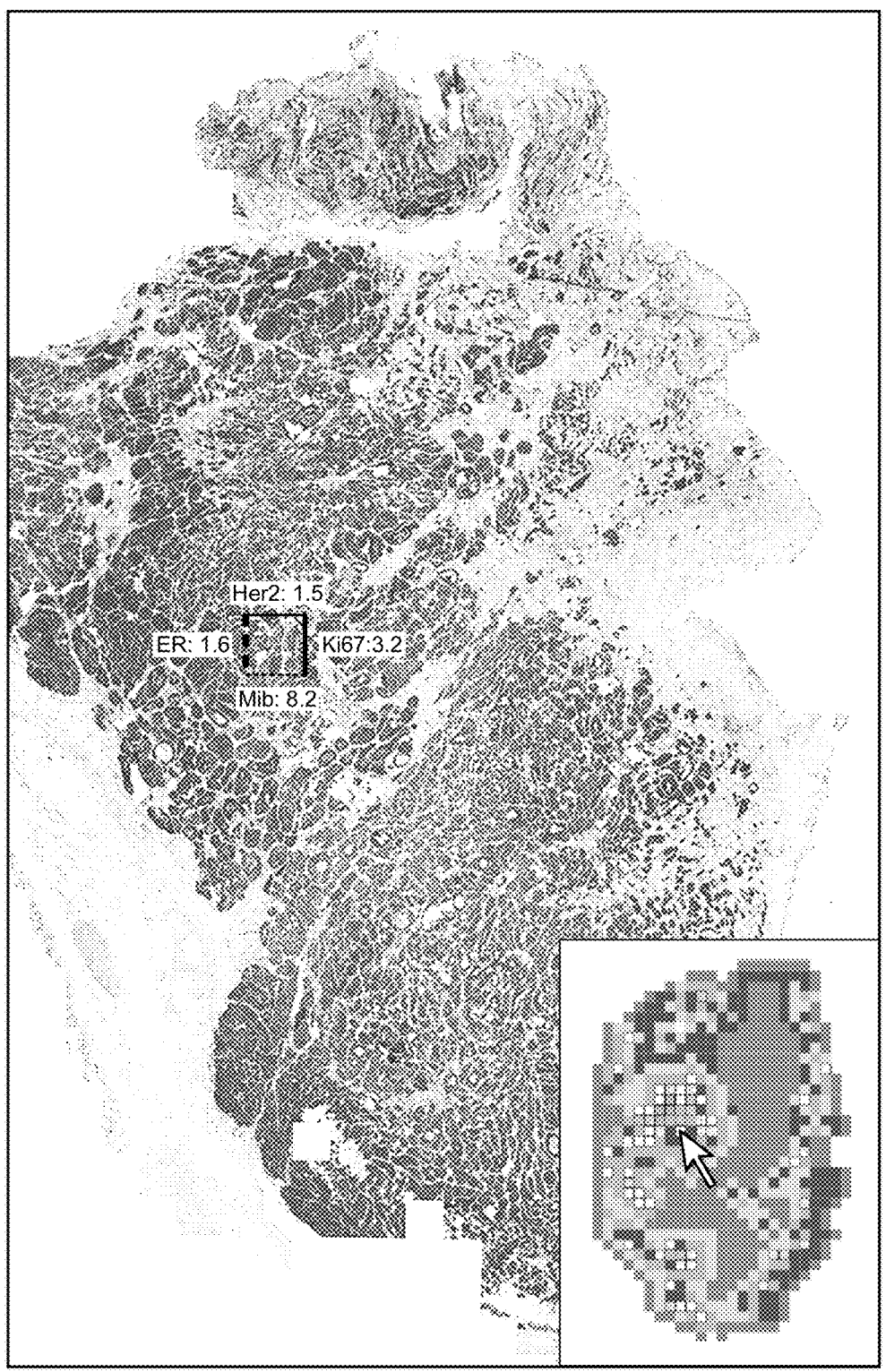
FIG. 15 is a screenshot of a graphical user interface displaying an image of a stained tissue slice and a combined hyperspectral image that combines the results of four other hyperspectral images.

FIG. 15 is a screenshot of the graphical user interface of the CNT system displaying a combined hyperspectral image (heat map) with false-color encoding in the frame at the lower right of the screen. In the embodiment of FIG. 15, the combined hyperspectral image combines the results of four other hyperspectral images. The results of the four other hyperspectral images are obtained by performing image analysis on the images of four tissue slices each stained with a different biomarker. For each stained slice, measurements are then taken using the objects of the data network obtained from the image analysis. In the embodiment of FIG. 15, the four tissue slices are stained with estrogen receptor (ER) stain, Mib, cell proliferation marker Ki67 and human Epidermal growth factor Receptor 2 (Her2). The pixel of the combined hyperspectral image in the frame at the lower right at the tip of the cursor arrow corresponds to the tile outlined in the full-resolution image of one of the stained slices. Each of four corners of the tile has a different color or pattern corresponding to a score value for one of the biomarkers. In this example, the scores for the four biomarkers are ER: 1.6, Mib 8.2, Ki67 3.2 and Her2: 1.5. As the cursor points to a different pixel of the combined hyperspectral image, the tile outline in the full-resolution image moves to the corresponding tile, and the biomarker score values change to reflect the results of the image analysis at the new location. The physician or clinician can navigate to the most critical tiles by looking for a particular color of pixels in the combined hyperspectral image.

Figure 16:
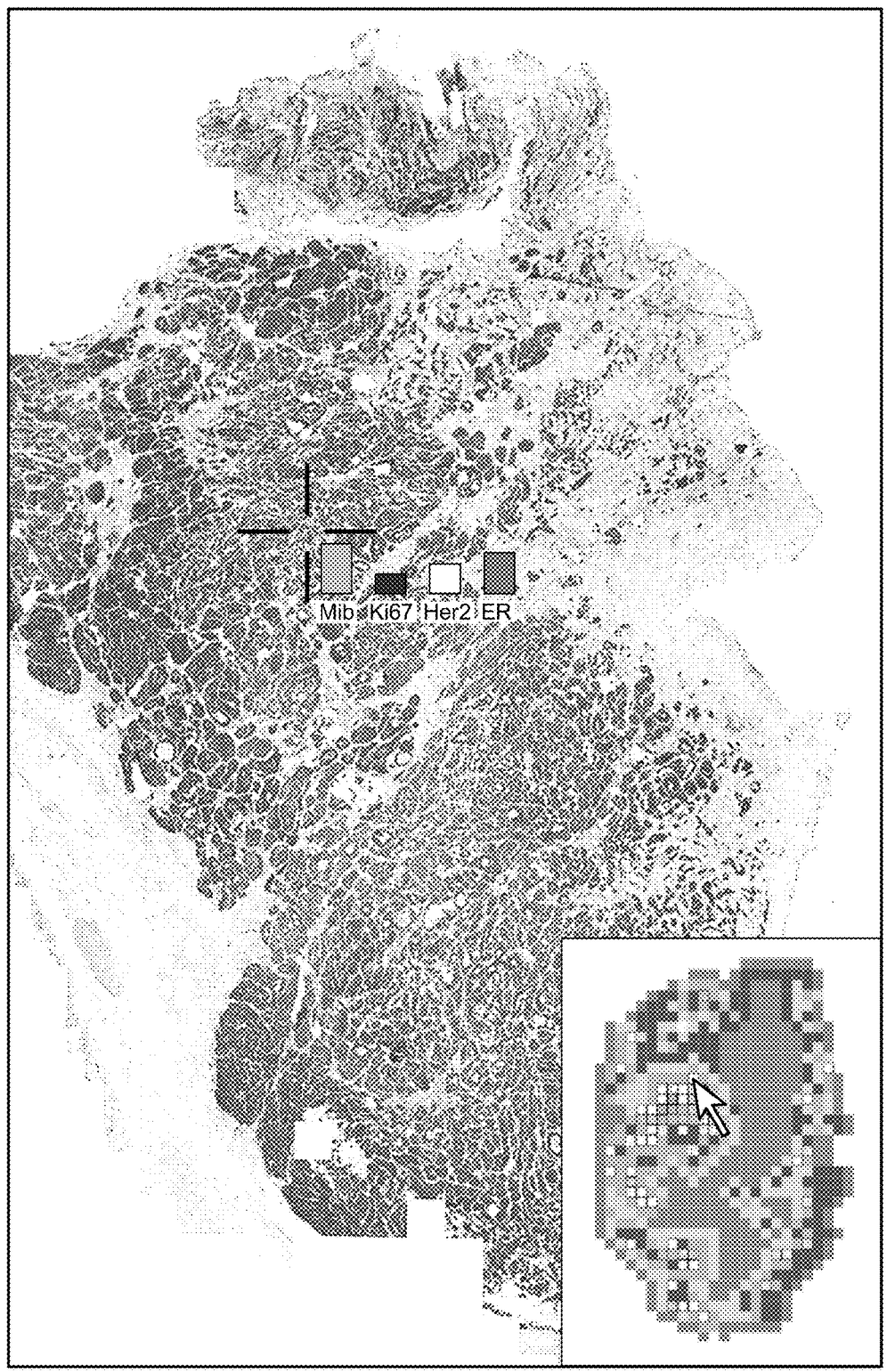
FIG. 16 is a screenshot displaying the combined hyperspectral image of FIG. 15 in which the square outline of a tile on the tissue slice in FIG. 15 has been replaced in by crosshairs centered over the middle of the tile.

FIG. 16 is a screenshot of the graphical user interface of the CNT system displaying the combined hyperspectral image together with a modified indicator of the tile and biomarker scores on the full-resolution image. The physician has navigated to a different pixel in FIG. 16. The square outline of the tile in FIG. 15 that corresponds to the hyperspectral pixel has been replaced in FIG. 16 by crosshairs centered over the middle of the tile. Instead of numerically listing the score values for the biomarkers, the magnitudes of the score values are represented by vertical bars.

Figure 17:
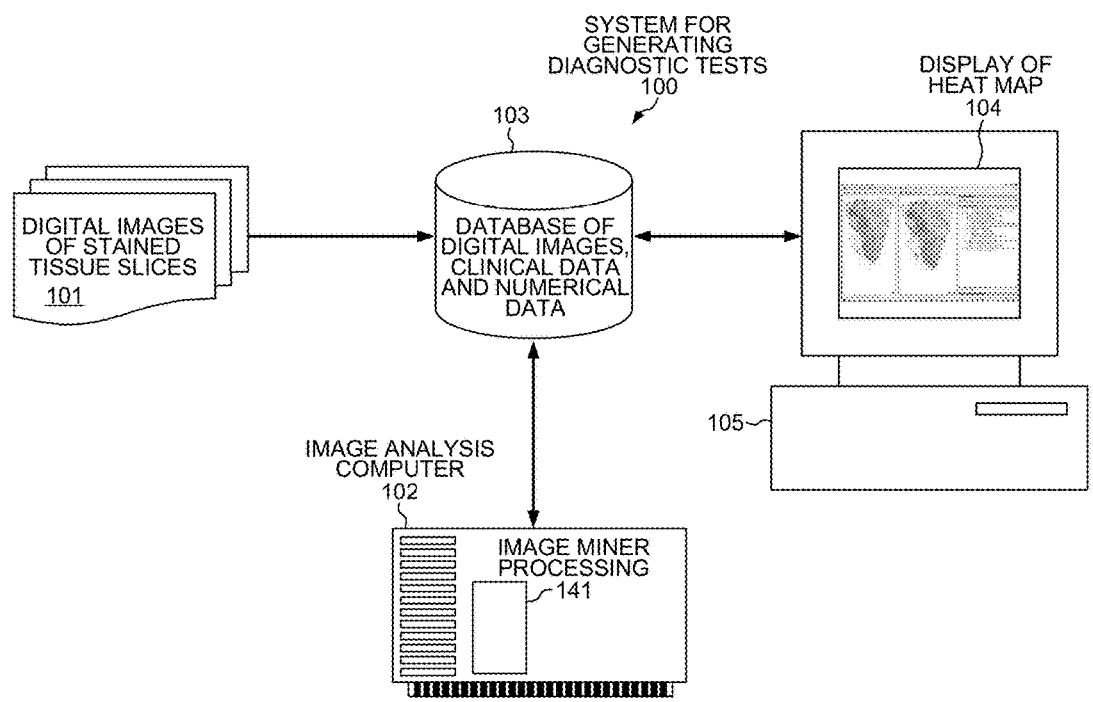
FIG. 17 is a diagram of a novel system that generates diagnostic tests by iteratively improving image and data analysis of coregistered tiles.

FIG. 17 shows an embodiment of the Cognition Network Technology (CNT) system 100 that is used to generate image-based diagnostic tests by optimizing the image analysis and data mining performed on coregistered images. For example, system 100 optimizes the rule sets used for image analysis and for calculating numerical data from analyzed images in order to improve the correlation between actual clinical outcomes of patients and the predicted outcomes based on images of tissue samples of the patients. The input to system 100 is digital images 101 of tissue slices that are stained by protein and receptor biomarkers and stains. Clinical data for the patients whose tissue samples are being analyzed are also input into system 100. For example, such clinical data includes the observed disease free survival time (DFS), overall survival time (OS) and the cancer recurrence time for the patients, as well as the response to a specific therapy, such as an adjuvant cancer therapy. The digital images 101 are acquired from the stained tissue samples. System 100 then performs various iterations of image and data analysis algorithms on the digital images. An image analysis computer 102 performs the classification, segmentation and quantification steps of the image analysis and data mining. The image processing is performed by computer-executable instructions stored on a computer-readable medium, such as a hard disk, a flash memory card or a CD. The digital images, as well as the numerical data obtained from analyzing the images, are stored in a database 103. For example, the "immunoscore" is an image-based diagnostic test for the severity of cancer, such as colorectal cancer. The immunoscore is used to predict disease-free, disease-specific and overall survival times of cancer patients. The immunoscore measures the response of the patient's immune system to the tumor cells based on the location, density and functional orientation of different types of immune cells, such as macrophages, dendritic cells, mast cells, natural killer cells, lymphocytes, B cells and T cells. System 100 is used to obtain rule sets for image analysis and data mining that implement an improved immunoscore diagnostic test. The rule sets defining the improved immunoscore diagnostic test are also stored in database 103. The heat maps or hyperspectral images that are generated during the optimization process of the image-based diagnostic test, such as the immunoscore, are displayed to the user of system 100 on a graphical user interface 104, such as the screen of a personal computer 105.

Figure 18:
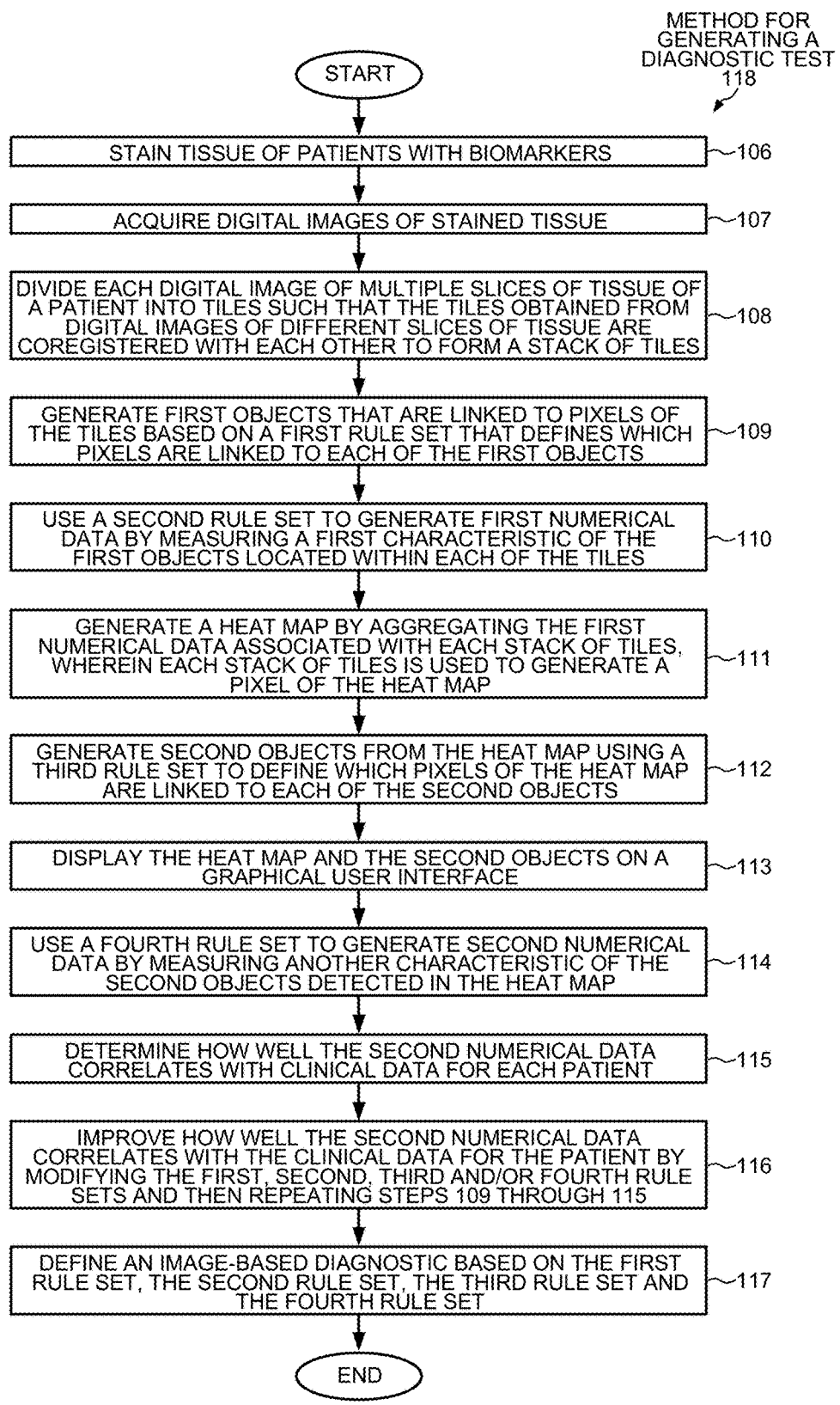
FIG. 18 is a flowchart of steps of a method for generating an image-based diagnostic test by iteratively improving image and data analysis of coregistered tiles.

FIG. 18 is a flowchart of steps 106-117 of a method 118 by which system 100 generates an image-based diagnostic test. In a first step 106, slices of tissue of a group of patients are stained with biomarkers that are proteins, receptors, antibodies or stains. The tissue slices that are to be stained are taken from each live patient in the form of a biopsy, which is then sliced into many slices. The planar slices are adjacent to one another and are located at the same position of the tissue sample in the x and y dimensions. The patients are all known to have had the same type of cancer, such as colon, breast or lung cancer. In addition, it is known if and when each patient has died and whether the patient is or became disease free. The biomarkers used to stain the tissue could include, for example, hematoxylin and eosin (H&E), phospho-histone H3 (PHH3) mitotic marker, Human Epidermal growth factor Receptor 2 (HER2), cytokeratin 18 (CK18) cytoplasmic stain, cell proliferation marker Ki67, estrogen receptor (ER) stain, progesterone receptor (PR) stain, cluster of differentiation 44 (CD44) antibody stain, CD23 antibody stain or immunohistochemically staining with protein-specific antibodies. In step 107, each stained slice of tissue is digitized using a digital microscope or a tissue slide scanner, and the resulting digital images are stored in database 103.

Figure 19:
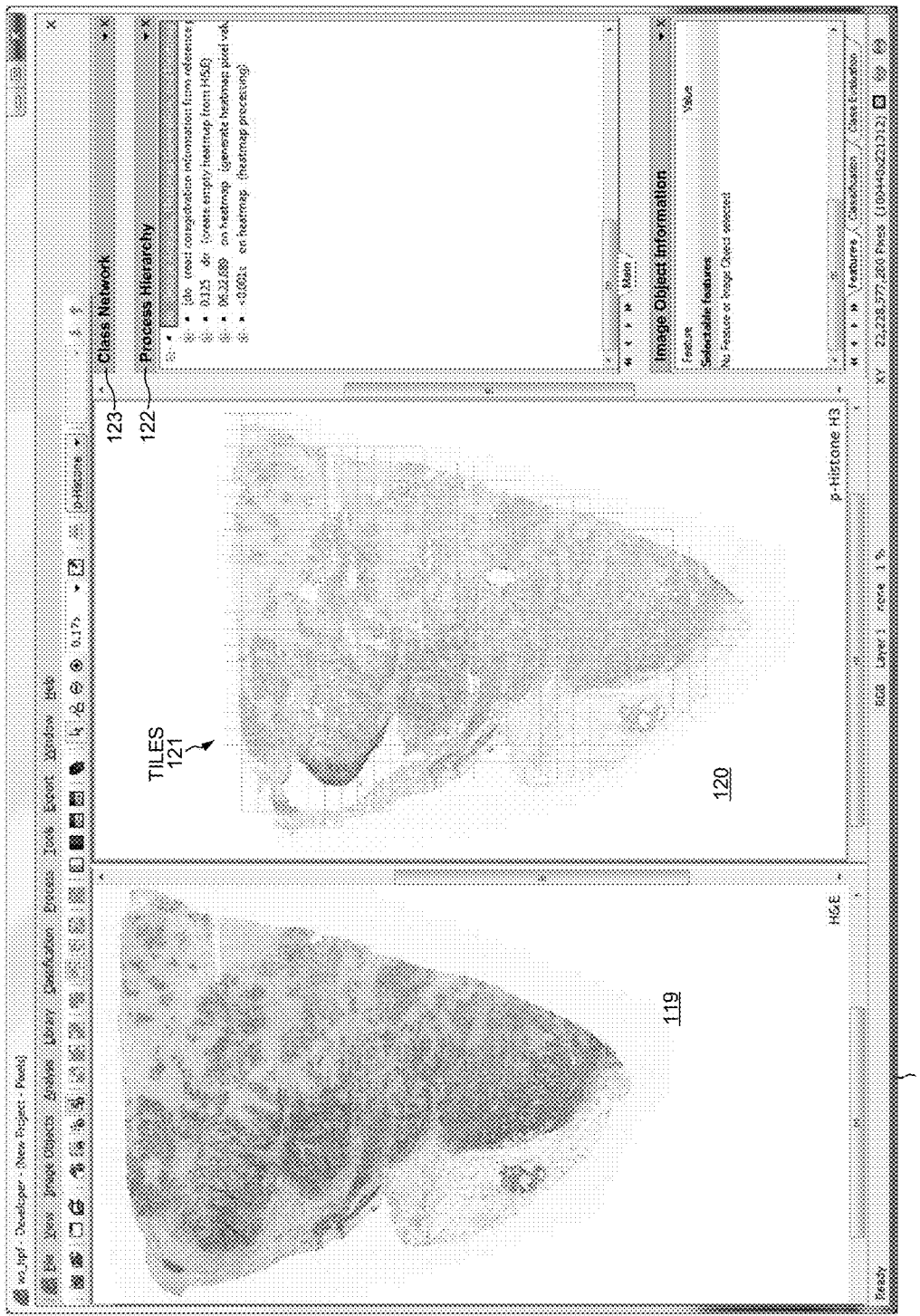
FIG. 19 is a screenshot displaying higher resolution digital images of two stained slices of cancer tissue.

FIG. 19 is a screenshot of the graphical user interface 104 of the CNT system 100 displaying higher resolution digital images of two stained slices of tissue from a patient with colorectal cancer. A first higher resolution digital image 119 is displayed at the left of the graphical user interface, and a second higher resolution digital image 120 is displayed in the center of the graphical user interface. First digital image 119 shows a first tissue slice that has been stained with the biomarker hematoxylin and eosin (H&E). Second digital image 120 shows a second tissue slice from the same biopsy that has been stained with the mitotic marker phospho-histone H3 (PHH3).

In step 108, each digital image of the slices of tissue from each patient is divided into tiles. FIG. 19 shows how second higher resolution digital image 120 has been divided into tiles 121. First digital image 119 is also divided into tiles, but those tiles are not shown in FIG. 19. The higher resolution images 119-120 can be coregistered with one another, or corresponding tiles in different digital images can be coregistered with each other. In this embodiment, corresponding landmarks in the two higher resolution digital images 119-120 are identified, and then those landmarks are used to coregister corresponding pairs of tiles. Thus, each of the tiles 121 in second image 120 is coregistered with its corresponding tile in first image 119 as well as with other tiles from images of other tissue slices. The coregistered tiles from the different images form stacks of tiles.

Coregistering tiles as opposed to entire digital images reduces the problem caused when tissue slices bend, stretch and become generally distorted. Because of distortions in individual slices, it might not be possible to coregister two full images without compensating for the distortion by stretching the images. The amount of distortion in any one tile is proportionately small, so two tiles can be coregistered with one another by just translating (shifting), rotating and/or flipping the tiles without having to stretch or rescale the tiles.

In step 109, first objects are generated that are linked to pixels of the tiles. A first rule set defines which pixels are linked to each of the first objects. For example, the first rule set is composed of image analysis algorithms for segmenting image objects and classifying those image objects. The first rule set is adapted to detect objects in the tiles based on the type of staining applied to the slice of tissue. The first objects are defined as elements of a hierarchical data network, such as data network 88 of FIG. 13. System 100 generates the data network by selectively linking pixels from each coregistered tile to image objects according to the first rule set, which is structured in the CNT software as a process hierarchy 122 and a classification network 123. The steps and algorithms of the process hierarchy 122 and the classes and subclasses of the classification network 123 are shown in panes towards the right of graphical user interface 104.

Figure 20:
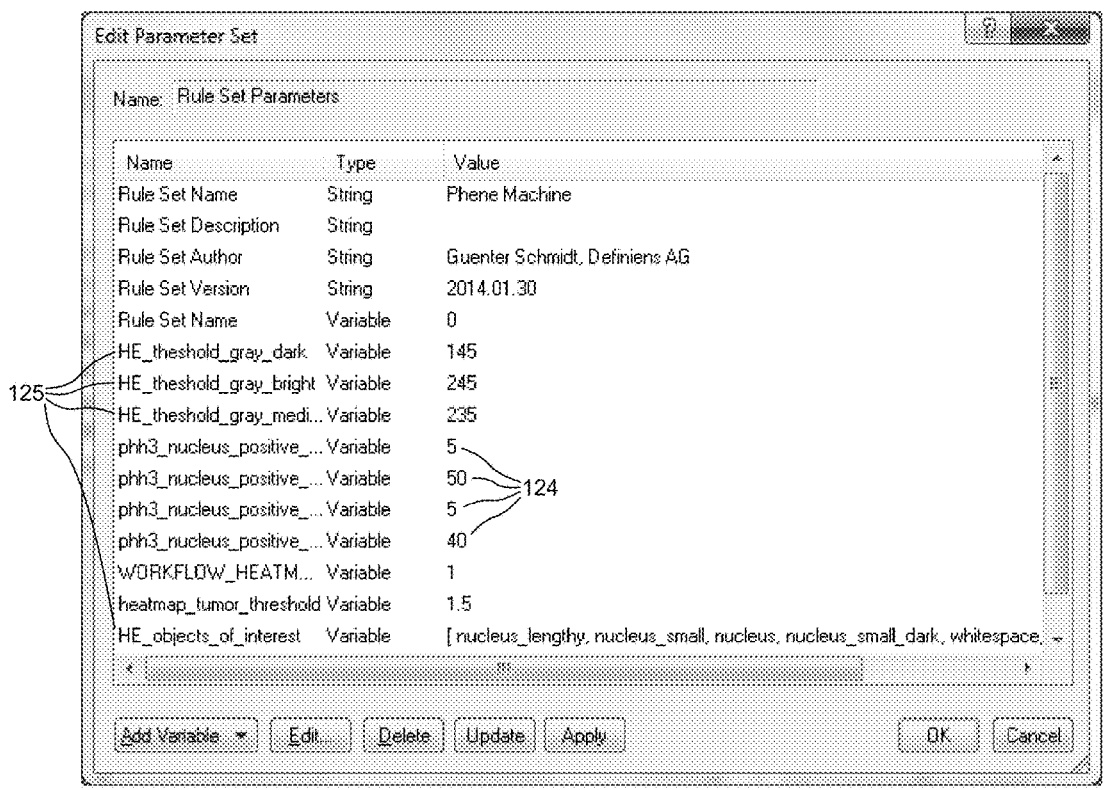
FIG. 20 shows a pop-up window listing segmentation and classification parameters of a rule set used to generate first image objects of a tile.

FIG. 20 shows a pop-up window listing some of the parameters of the first rule set, named "Phene Machine". Image analysis is performed on each tile of the stacks of coregistered tiles using the parameters of the first rule set. Tiles 121 were obtained from the second image 120 that was stained with PHH3, whereas other tiles resulted from the first image 119 that was stained with H&E. Some of the first objects are generated based on parameters 124 for how the tissue was stained by PHH3, and other first objects are generated based on other parameters 125 for how the tissue was stained by H&E. For example, some of the first objects represent clusters of tumor cells of colorectal cancer. The first objects in the class of tumor regions are linked to pixels that make up more than a predetermined proportion of the pixels within a defined area and whose colors fall within a selected color range associated with the H&E stain. The pop-up window of FIG. 20 indicates that the parameters 125 for the selected color ranges for dark, medium and bright H&E stained pixels are 145, 235 and 245 respectively. The first objects are also generated based on the pixels that have the color of the PHH3 stain, which marks mitotic (dividing) nuclei. A high degree of cell division tends to indicate cancerous growth. Other parameters not shown in FIG. 20 are used to generate objects associated with immune cells. In another embodiment, instead of staining using immunohistochemistry (IHC), the tissue is stained using immunofluorescence (IF) to quantify the protein expression. In another embodiment, multiple proteins on a single slice are stained using corresponding multiple dyes, whereas each dye absorbs/emits light at specific wavelengths (colors) using IHC/IF.

Figure 21:
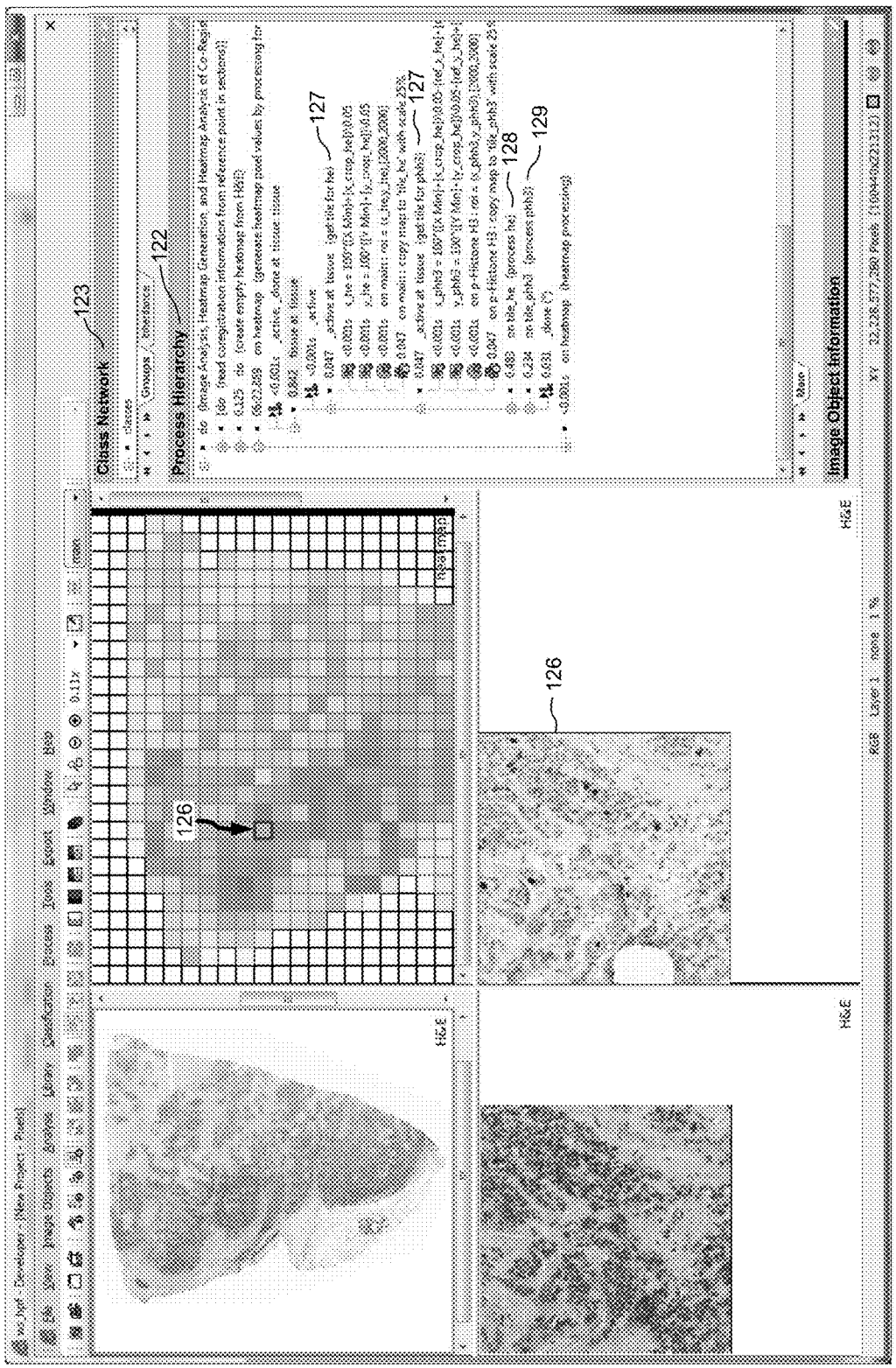
FIG. 21 is a screenshot showing a tile in which those first objects that correspond to nuclei have been marked with a dark color.

FIG. 21 is a screenshot of the graphical user interface 104 of the CNT system 100 showing a tile 126 in the lower central pane in which those first objects that correspond to nuclei have been marked with a dark color. The lower left pane in the screenshot shows the portion of first higher resolution image 119 that is included in tile 126. The process hierarchy 122 of the first rule set is shown in the center pane at the right. Step 108 of dividing the digital images 119-120 into tiles is performed by levels 127 of the process hierarchy. Step 109 of generating the first objects is performed by levels 128-129. Level 128 generates first objects in tile 126 using the H&E stained first image 119, and level 129 generates first objects in tile 126 using the coregistered tile portion of the PHH3 stained second image 120. CNT system 100 indicates the location of tile 126 in the upper central pane of the screenshot with a thicker frame around the tile.

In step 110, system 100 uses a second rule set to generate first numerical data by measuring a first characteristic of the first objects located within each of the tiles. Examples of characteristics of objects that are quantified by the first numerical data are (i) average area of the nuclei in a tile, (ii) average maximum length (diameter) of the nuclei, (iii) average number of nuclei in each cluster of nuclei, (iv) staining intensity of nuclei having less than average length, (v) average distance between clusters of nuclei, and (vi) average distance between the closest tumor cells and immune cells in a tile.

Figure 22:
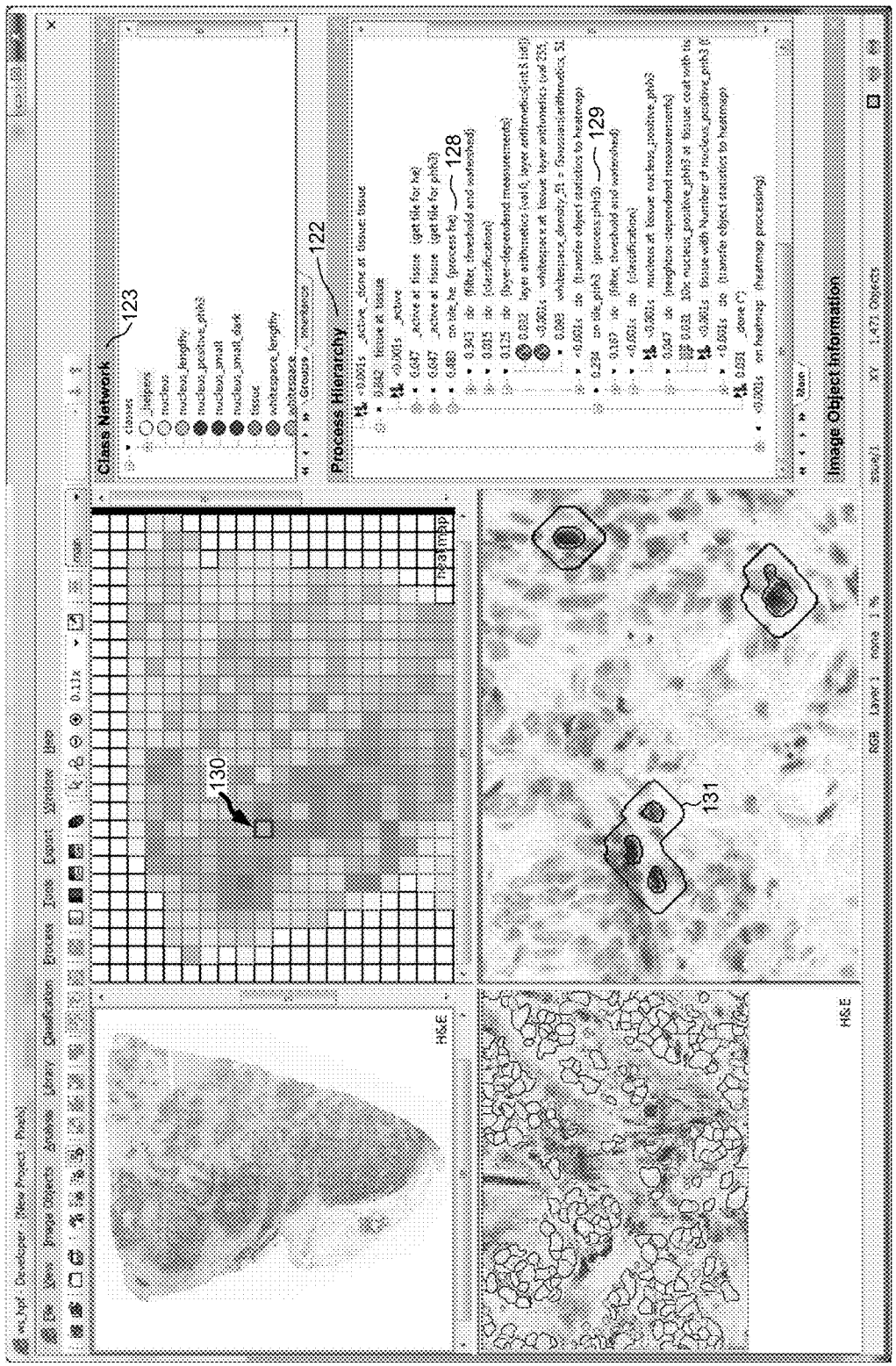
FIG. 22 is a screenshot showing a more detailed view of first objects detected in a tile.

FIG. 22 is a screenshot showing first objects in the lower left and central panes of the graphical user interface 104. The first objects belong to a tile 130 indicated in the upper central pane. For example, the first objects that are segmented and classified in the lower central pane are used to generate numerical data based on characteristics of the first objects as determined using the second rule set. A cluster 131 of three tumor cells stained with H&E has been detected that includes mitotic nuclei stained with PHH3. Thus, tile 130 includes image analysis information both from the H&E stained layer and from the PHH3 stained layer of the stack of image layers that make up the tile. The first objects of tile 130 can be used to quantify the amount of nucleus clustering per defined area of the H&E stained tissue and to calculate the number of mitotic objects in the identified colorectal tumor cells.

Figure 23:
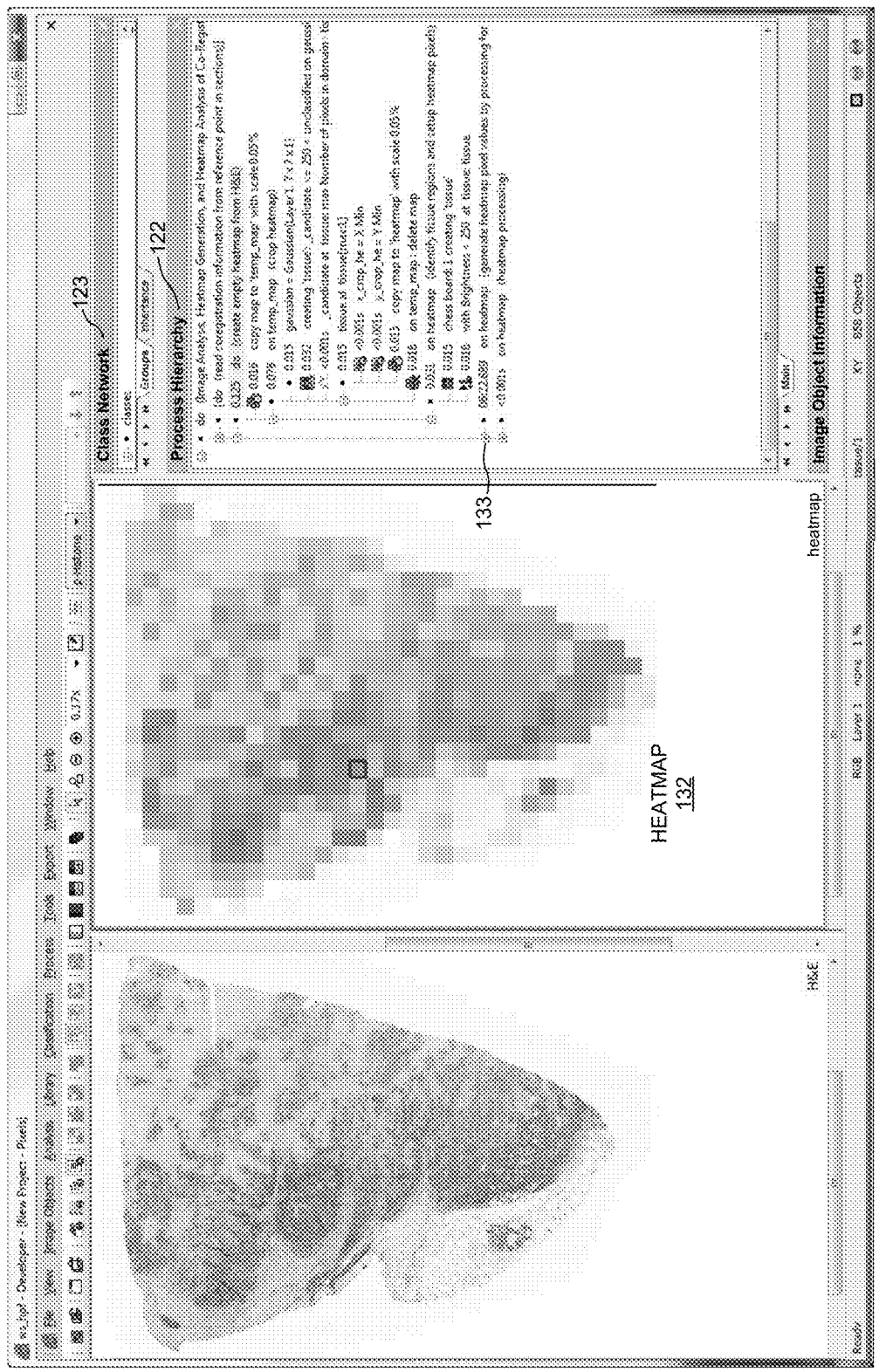
FIG. 23 is a screenshot showing a heat map in which individual pixels of the heat map are assigned a color or shade of gray based on first numerical data aggregated from all of the coregistered tiles in the stack of tiles.

In step 111, system 100 generates a heat map by aggregating the first numerical data associated with each stack of coregistered tiles. FIG. 23 shows a heat map 132 in which individual pixels of the heat map are assigned a gray value or color based on the value of the numerical data aggregated from all of the tiles in the stack of tiles. Thus, each stack of tiles is used to generate a pixel of heat map 132. Heat map 132 is a hyperspectral image that is displayed on graphical user interface 104 using a false-color encoding of the numerical data from the stack of tiles that comprises each pixel. Step 111 of generating heat map 132 is performed by level 133 of process hierarchy 122, as shown in the center pane at the right in FIG. 23. Process hierarchy 122 can be expanded, and the substeps of level 133 of the CNT software can be viewed when the "+" is clicked by the user to the left of the description, "generate heatmap pixel values by processing for each pixel".

In another embodiment, individual pixels of the heat map are not generated based on numerical data derived solely from within tiled regions of the higher resolution images. In this embodiment, statistical tiles as opposed to regional tiles are used. The objects used to generate the numerical data using regional tiles are located only within tiled regions that do not overlap. On the other hand, the numerical data obtained using statistical tiles is not derived solely from non-overlapping rectangular regions on the higher resolution images. Image information used to derive the data for one statistical tile may also be considered to derive data for another statistical tile. For example, numerical data may indicate the tumor probability in a local area, where the contribution of the image information to the numerical data decreases with increasing distance from the center of the statistical tile. In another example, numerical data for each statistical tile may indicate the number of nuclei in larger overlapping regions of the higher resolution image. In the embodiment in which statistical tiles as opposed to regional tiles are used, step 108 is skipped in which the higher resolution images 120 are divided into tiles 121. Heat map 132 is then generated in step 111 by downscaling an image layer of statistical tiles. Pixels of the heat map 132 generated with statistical tiles, however, represent more comprehensive image information as opposed to numerical data associated only with discrete, non-overlapping tiled regions of the higher resolution images. In yet another embodiment, regional tiles are used, but the first numerical data generated in step 110 is derived not just from first objects located within one tile, but also from first objects located in adjacent tiles.

In step 112, system 100 generates second objects from the heat map using a third rule set. The third rule set defines which pixels of the heat map are linked to each of the second objects of an additional hierarchical data network. For example, a tumor class of second objects could be formed by linking those objects to pixels of the heat map that have a false color or gray value that falls within a selected color range. The false color is not a stain color, but rather an artificially assigned color based on the numerical data obtained by measuring characteristics of objects recognized in the layers of tiles that make up each pixel.

Figure 24:
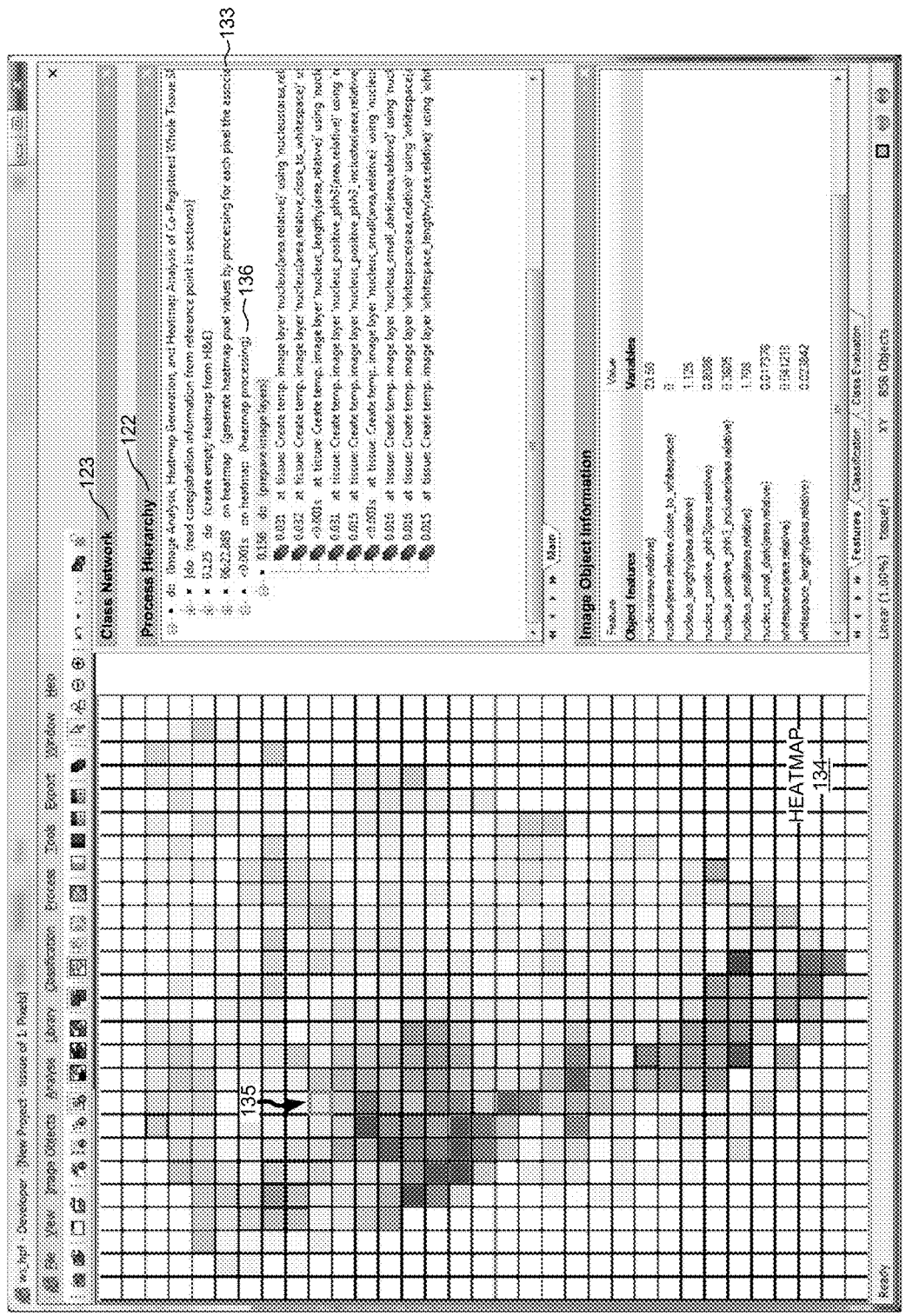
FIG. 24 shows a heatmap in which the pixel color depends on a predetermined combination of characteristics of the first objects in the coregistered tiles that make up each pixel.

FIG. 24 shows a heatmap 134 generated in step 111 in which the color of each pixel depends on a predetermined combination of characteristics of the first objects in the coregistered tiles that make up each pixel. For example, the values of selected characteristics of the first objects in a highlighted pixel 135 are listed in the lower right pane of the screenshot of FIG. 24. Step 112 is then performed by linking second objects to selected pixels that were defined in step 111. Step 112 for generating the second objects on heat map 134 is performed by level 136 of process hierarchy 122, as shown in the center pane at the right in FIG. 24.

Figure 25:
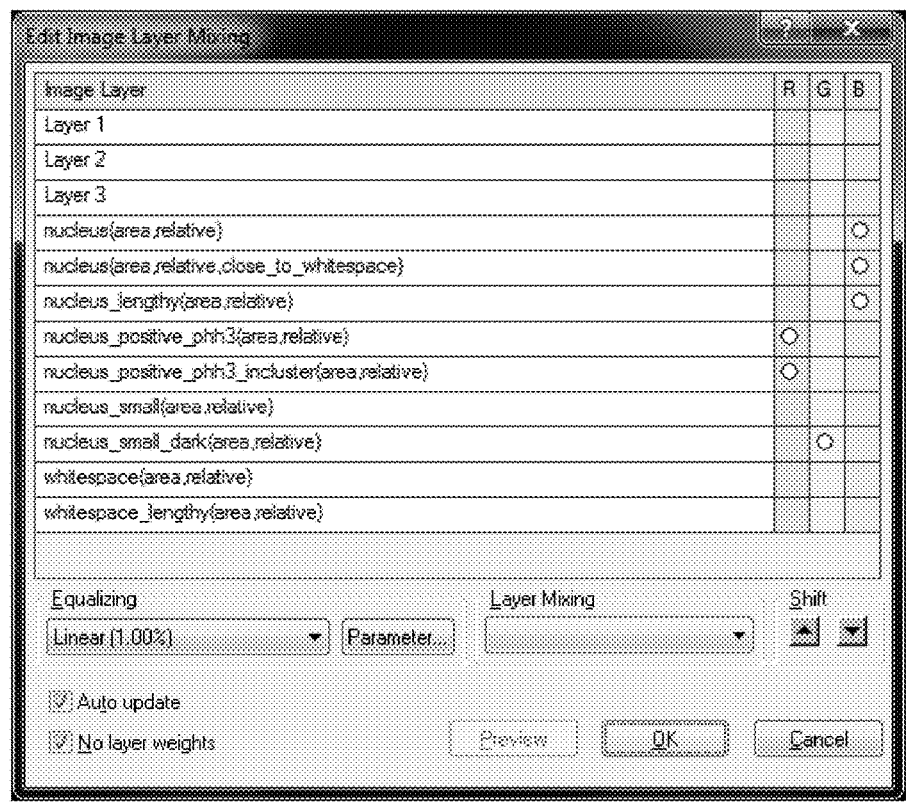
FIG. 25 is a pop-up window that lists the selected characteristics of the first objects that are used to assign a false color to each pixel of the heatmap of FIG. 24.

FIG. 25 is a pop-up window displayed by system 100 that lists the selected characteristics of the first objects that are used to assign a false color to each pixel of heatmap 134. FIG. 25 shows that values indicating a large size of nuclei contribute to a bluer hue of each pixel. Nuclei that are more clustered and stained more by PHH3 contribute to a redder hue of each pixel. And nuclei that are smaller and stained more by H&E contribute to a greener hue of each pixel. The combined contribution of the red, green and blue hues determines the false color of each pixel.

Figure 26:
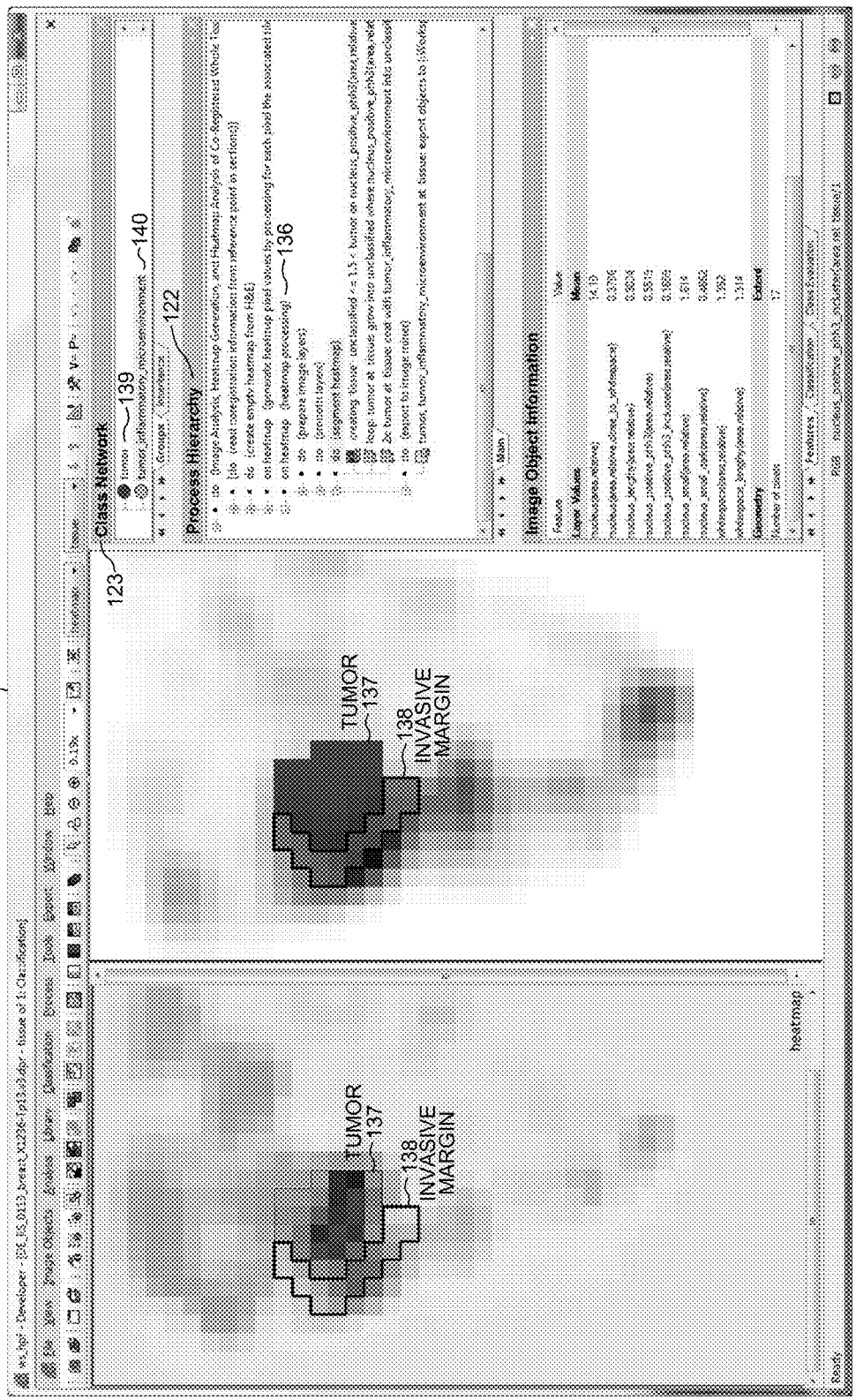
FIG. 26 is a screenshot displaying second objects on a heat map generated using a third rule set.

In step 113, the heat map and the second objects are displayed on the graphical user interface 104. FIG. 26 is a screenshot of the graphical user interface 104 of the CNT system 100 displaying two of the second objects 137-138 generated in step 112. The segmentation and classification algorithms of the third rule set are chosen so that object 137 best identifies the region of the colorectal cancer cells and object 138 best identifies the inflamed invasive margin of immune cell populations, including lymphocytes, B cells and T cells, around the cancer cells. Classification network 123 in the upper right pane of FIG. 26 classifies object 137 as belonging to the class "tumor" 139. Object 138 is classified as belong to the class "tumor_inflammatory_micro-environment" 140, which designates the invasive margin. The location, density and functional orientation of the different immune cell populations in the invasive margin is later correlated to the disease free survival time (DFS) or the overall survival time (OS) of each of the patients from whom the tissue samples were taken.

In step 114, system 100 uses a fourth rule set to generate second numerical data by measuring a characteristic of the second objects detected in the heat map 134. Examples of characteristics of the second objects that are quantified by the second numerical data include (i) the area of the tumor region, (ii) the area of the invasive margin, (iii) the area of the invasive margin relative to the area of the tumor, (iv) the width of the invasive margin, and (v) the mean pixel intensity of the group of second objects detected in the heat map that are combined to form the tumor region. For example, it is apparent from FIG. 26 that tumor object 137 has an area of twenty-eight pixels and that invasive margin object 138 has an area of seventeen pixels. So the characteristic (iii) of the relative areas would be 0.607 (17 pixels/ 28 pixels).

Figure 27:
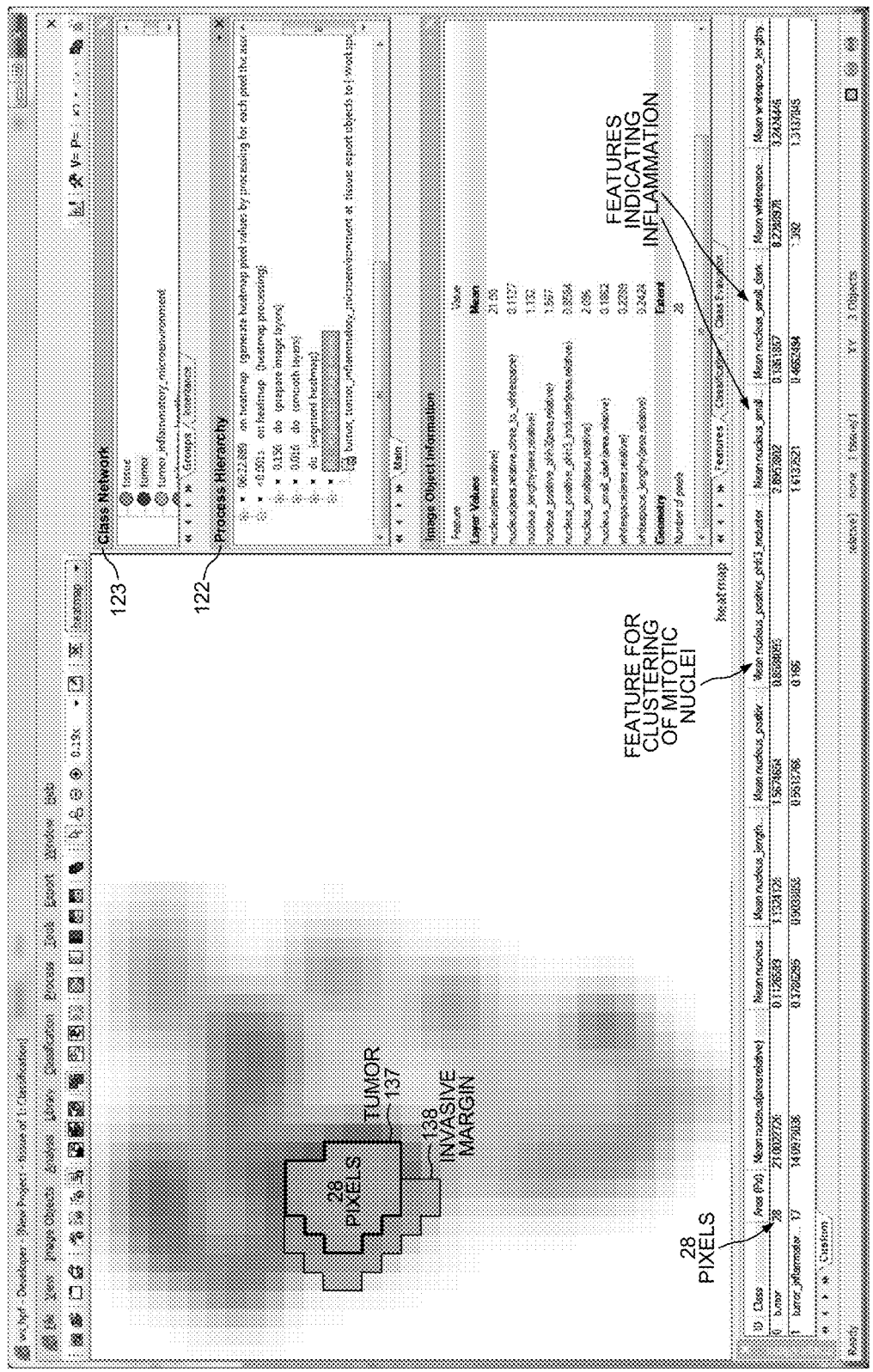
FIG. 27 is a screenshot displaying the second numerical data generated from the second objects using a fourth rule set.

FIG. 27 is a screenshot of graphical user interface 104 displaying in the bottom pane the second numerical data generated in step 114. The bottom pane lists second numerical data such as the area of the tumor object (28 pixels), the area of the inflamed invasive margin (17 pixels), the clustering characteristic "Mean nucleus_positive_phh3_incluster" of the nuclei in the tumor (0.8584093) and of the nuclei in the invasive margin (0.166), the inflammation characteristic for small nuclei "Mean nucleus_small" in the tumor (2.0957802) and in the invasive margin (1.6137521), and the inflammation characteristic for small and dark nuclei "Mean nucleus_small_dark" in the tumor (0.1861857) and in the invasive margin (0.4662494). The bottom pane also includes first numerical data such as the mean area of nucleus objects in the tumor region (21.0022720) and in the later determined region of the invasive margin (14.0973036) and the mean length of the nucleus objects in the tumor region (1.1324128) and in the later determined region of the invasive margin (0.9033855). After the second numerical data is generated in step 114, both the second numerical data and the first numerical data is sent to the image mining processing functionality 141 of the Cognition Network Technology system 100 for further analysis and optimization.

In step 115, system 100 determines how well the second numerical data correlates with clinical data for the patient whose tissue samples where analyzed. For example, the second numerical data is used to generate an immunoscore based on the number, type and location of immune cells, such as lymphocytes, B cells and T cells, in the invasive margin. But first the second numerical data is used to define the region of the invasive margin and of the tumor so that the cells in those regions can be characterized. A particular immunoscore plus other patient information is then used to predict clinical outcomes for each patient, such as the disease free survival time (DFS) and the overall survival time (OS) for the patient. The immunoscore predicts the DFS for a patient with colorectal cancer at the time of surgery that removes the cancer and when no distant metastasis is detectable. Thus, the immunoscore predicts the recurrence of colorectal cancer in these patients. The immunoscore ranges from zero to four. When low densities of the immune cells are detected in both the tumor and in the invasive margin, the immunoscore is zero. When high densities of the immune cells are detected in both the tumor and in the invasive margin, the immunoscore is four. The immunoscore predicts that patients with a high immunoscore will have a lower recurrence of cancer and higher disease free and overall survival times. For example, empirical studies might show that patients with an immunoscore of four have a 5% chance of a recurrence of cancer and an 85% chance of being alive after five years. Conversely, studies might show that patients with an immunoscore of zero have a 70% chance of a recurrence of cancer and a 25% chance of being alive after five years.

In step 115, the image mining functionality 141 of system 100 generates an immunoscore for each patient and compares the predicted disease free survival time (DFS) to the actual survival times for each patient in the group whose tissue samples were stained in step 106. System 100 determines that the second numerical data does not correlate well with the clinical data of a patient if the immunoscore generated with the second numerical data predicts a disease free survival time that is significantly different than the observed survival time for the patient. System 100 determines the quality of the correlation between the second numerical data and the clinical data for each patient in the group of patients whose tissue samples were analyzed.

Another measurement of the quality of the correlation between the second numerical data and the actual clinical data for a patient is the p-value of the Kaplan-Meier analysis when comparing two groups of patients. One group represents patients who have long disease free survival times (DFSs), and the second group represents patients who have short DFSs. A low p-value indicates a significant separation of the two groups when the DFSs are plotted on a Kaplan-Meier graph. Second numerical data that predicts DFSs that fall within separate groups of short-lived and long-lived patients correlates well with the actual clinical data for those patients.

In step 116, system 100 improves how well the second numerical data correlates with the clinical data for the patient by modifying the first rule set, the second rule set, the third rule set and the fourth rule set and then repeating steps 109 through 115. The rule sets are modified in a manner that reduces the computational resources required to repeat steps 109 through 115. The prognostic quality of the immunoscore depends on accurately detecting both the edge of the tumor as well as the width of the invasive margin. By modifying the first rule set, the first objects will be segmented in a different manner that can be combined to more accurately detect the tumor. For example, the first rule set may indicate what range of gray values of pixels should be linked together to form objects representing tissue stained by H&E. By modifying the second rule set, the calculation of the first characteristic of the segmented first objects will be different so that different segmented first objects will be combined together to form the tumor object. Similarly, the stained tissue in the invasive margin will be segmented and classified differently by modifying the first rule set. And the determination of which first objects are combined together to form the invasive margin will be different if the second rule set is modified and the first characteristic is calculated differently.

Figure 28A:
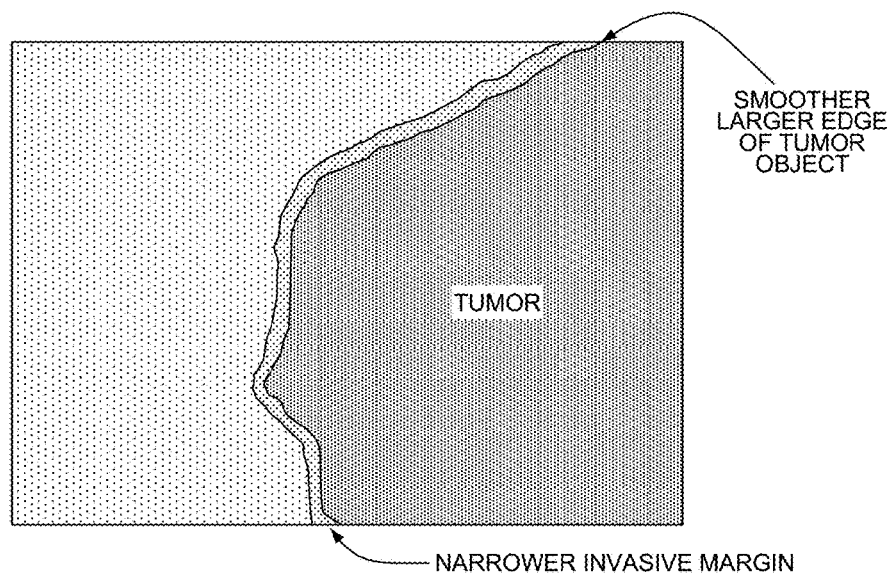
FIG. 28A and FIG. 28B illustrate two different ways of segmenting and classifying first objects and of combining those first objects to form a tumor region and an invasive margin region.
Figure 28B:
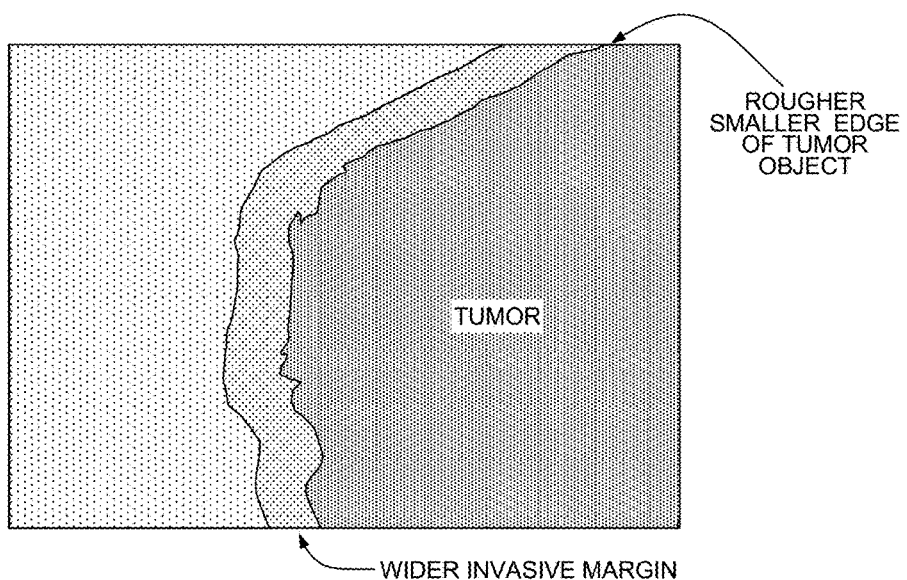

FIGS. 28A-B show two different ways of segmenting and classifying first objects and of combining those first objects to form the tumor region and the invasive margin. For example, after the first iteration of steps 109-110, system 100 may generate a tumor object and an invasive margin object as shown in FIG. 28A. Then after the first rule set and the second rule set are modified in step 116 and steps 109-110 are repeated, system 100 may generate tumor and invasive margin objects as shown in FIG. 28B. Note that the tumor object in FIG. 28B is smaller and has a rougher edge than the tumor object in FIG. 28A. Some of the cells that were considered as being part of the tumor object when using the original first and second rule sets were later designated as being part of the invasive margin when the first and second rule sets were modified. The rule sets are modified so as to improve the recognition of the cancer nuclei and of inflammation nuclei.

By modifying the third and fourth rule sets, the manner is changed in which the pixels of the heat map are segmented and classified and in which the second objects are combined. For example, the width in pixels of the invasive margin object 138 may vary if the third and fourth rule sets are modified. However, the width in pixels of the invasive margin object 138 may also vary if the first rule set is modified and the second through fourth rule sets are held constant because the underlying first objects used to generate the heat map will vary. The width of the invasive margin and the relative sizes of the invasive margin and tumor may change the resulting immunoscore. The rule sets are modified so that the numerical data used to derive the immunoscore and its associated prognostic clinical data better correlates with the observed clinical data for the group of patients.

Figure 29:
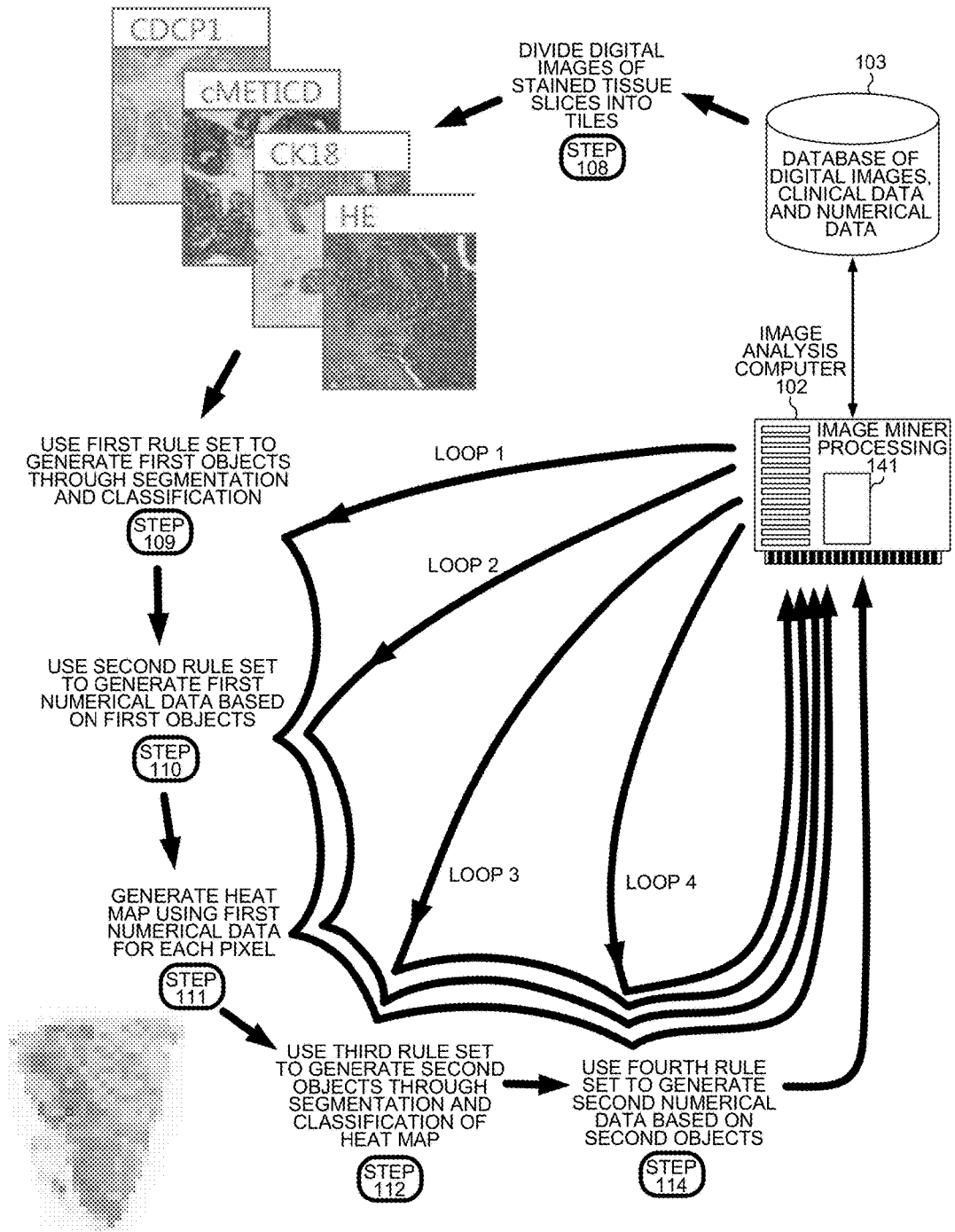
FIG. 29 illustrates the steps of a method for generating a diagnostic test by modifying rule sets to improve the correlation between numerical data and the actual clinical data of the patients whose digital images are being analyzed.

FIG. 29 illustrates the method 118 for generating a diagnostic test by modifying rule sets to improve the correlation between numerical data generated by system 100 and the actual clinical data for the patients whose digital images are being analyzed. All of the rule sets are not necessarily modified at the same time. In the optimization of the correlation, it is most efficient to modify those rule sets first that require less computational resources to generate new numerical data. For example, the least computational resources of image analysis computer 102 are required to generate just the second numerical data when only the fourth rule set is modified. In that case, only steps 114-115 are repeated, as illustrated by small loop 4 in FIG. 29. More computational resources are required to generate the first objects when the first rule set is modifies than when any other single rule set is modified. Even when the first rule set is modified and the other rule sets are not changed, all of steps 109 through 115 must still be repeated because the different first objects generated in step 109 result in different first numerical data in step 111, different second objects in step 112, and different second numerical data in step 114. When the first rule set is modified, regardless of whether any other rule sets are also modified, method 188 follows the large loop 1 in FIG. 29. The first, second, third and/or fourth rule sets are modified in step 116, and the appropriate steps are repeated as shown by the loops in FIG. 29 until the correlation between the actual clinical data for the patients and the generated numerical data that results in predicted clinical outcomes is improved by a desired amount.

In one embodiment, system 100 estimates the computational resources needed to execute steps 109 to 114 in order to achieve a desired correlation by modifying the first, second, third and/or forth rule sets. Typically, the second numerical data can be generated with less computational resources following a modification of just the fourth rule set compared to generating the second numerical data after modifying just the first rule set. The computational resources are measured in terms of both processing time and computer memory consumption.

In step 117, system 100 defines an image-based diagnostic test based on the first rule set, the second rule set, the third rule set and the fourth rule set. For example, system 100 defines an immunoscore based on the second numerical data which is generated when defined first, second, third and fourth rule sets are used to analyze digital images of tissue slices of a patient. The immunoscore can also be based on the first numerical data in addition to the second numerical data. The first and second numerical data listed at the bottom of FIG. 27 is sent to the image mining processing functionality 141, which then uses the data to calculate an immunoscore from zero to four.

An immunoscore defined by the rule sets optimized using method 118 results in a more consistent and accurate prognosis of survival times than does an immunoscore determined manually. A conventional immunoscore is determined by staining tissue slices with a stain for the tumor tissue as well as multiple stains for the inflamed tissue of the invasive margin. Then the pathologist manually draws the region of the invasive margin, the region of the tumor and a reference region. The score is determined based on these manually drawn regions. Regions defined using image and data analysis based on rule sets are more accurate and consistent over different patients than the manually drawn regions and, therefore, result in more accurate prognostic scores.

Although the immunoscore is an example of an image-based diagnostic test that can be generated using method 118, other diagnostic tests can also be defined based on the rule sets that are optimized using method 118. For example, an improved Allred score, an improved Gleason score, an improved Elston-Ellis score or an improved HercepTest score could also be defined based on the first, second, third and fourth rule sets. In another embodiment, an image-based diagnostic test that can be generated that predicts a probability that the patient will remain disease free for a predetermined period of time after a clinical action has been taken on the patient.

Figure 30:
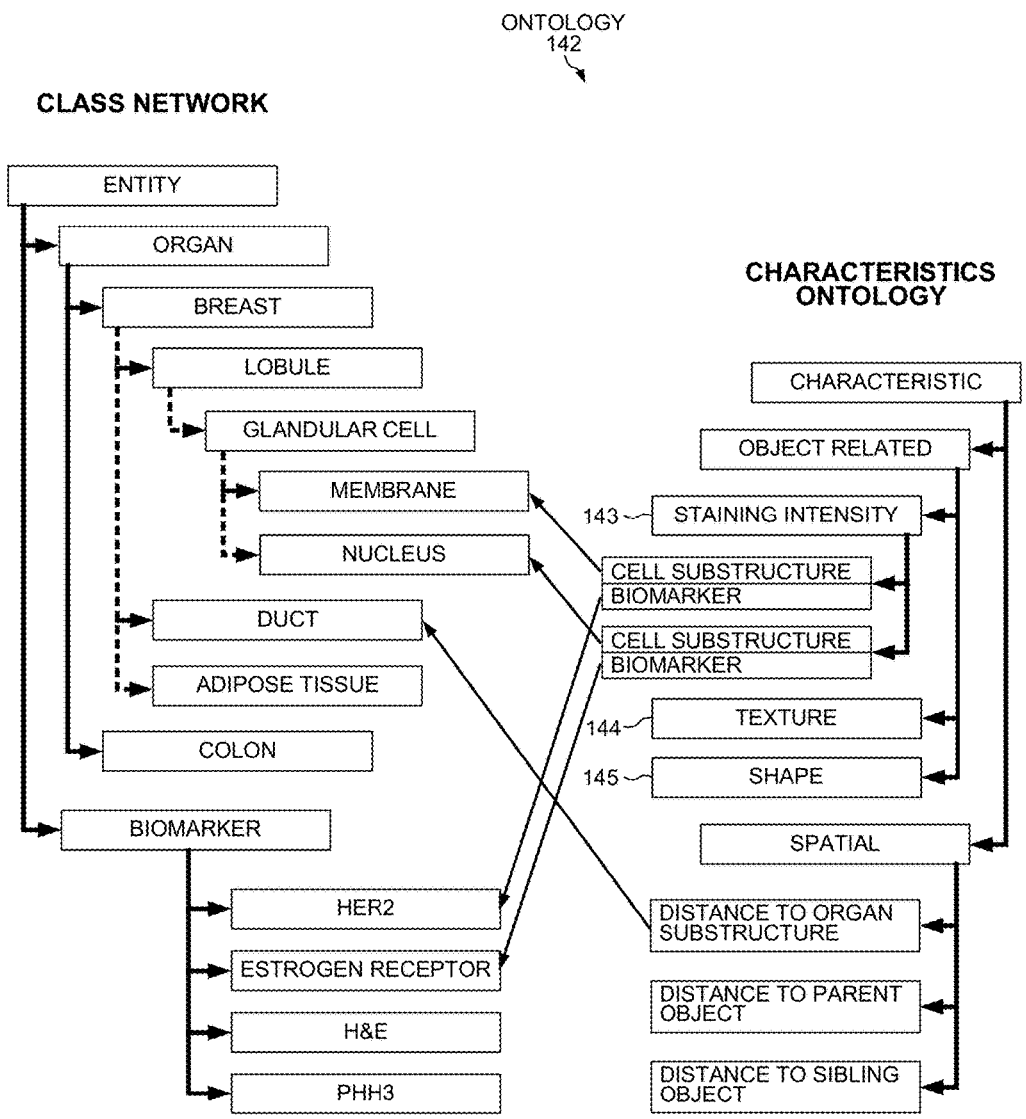
FIG. 30 is a diagram of an ontology that associates vocabulary of class network objects with characteristics describing those objects.

FIG. 30 illustrates one way of modifying the rule sets before repeating the classification, segmentation and quantification procedures of image and data analysis in steps 109 through 115. Method 118 uses an ontology 142 to determine how each rule set should be modified before the analysis in each of the loops 1-4 of FIG. 29 is performed. The ontology 142 structures the vocabulary of the objects in the hierarchical class network with characteristics that describe those objects and relationships between those objects. Examples of types of first characteristics that describe image objects are: shape, texture, composition, hierarchical context and neighbor context. Examples of shape characteristics are area, border length, diameter or maximum length, ellipticity and number of concave or convex points on the border. Texture can be measured as the granularity or the color distribution inside an object or at the border of the object. The composition of an image object measures subobjects, such as the average number of nucleoli in each nucleus or the average number of nuclei in each cluster of nuclei. The hierarchical context is the position of an object relative to a parent object, such as the distance from an object of immune cells to the center of a tumor object or the position of an object on the glandular epithelium. The neighbor context measures statistical properties of other objects in the vicinity of the object, such as the average distance between clusters of nuclei or the distance from an object to a similar object.

The ontology 142 links characteristics of objects to specific objects and subobjects based on expert knowledge, such as knowledge of how human tissue is organized or which biomarkers stain which tissues. Rule sets are modified in step 116 in an incremental manner based on the ontology before some or all of the analysis steps 109 through 115 are repeated. The incremental amount by which a rule set is modified is based on the shortest topological distance in the ontology between characteristics. For example, if ontology 142 is being use and the first characteristic of the first objects being measured in step 110 is the staining intensity 143, then the second rule set would be modified before the first repetition of step 110 so that the characteristic being measured is the texture 144 of the first objects. Then the second rule set would be modified before the second repetition of step 110 so that the characteristic being measured is the shape 145 of the first objects. Alternatively, the shortest topological distance along the ontology may be to the next sublevel of the staining intensity characteristic before proceeding to the texture characteristic.

Figure 31:
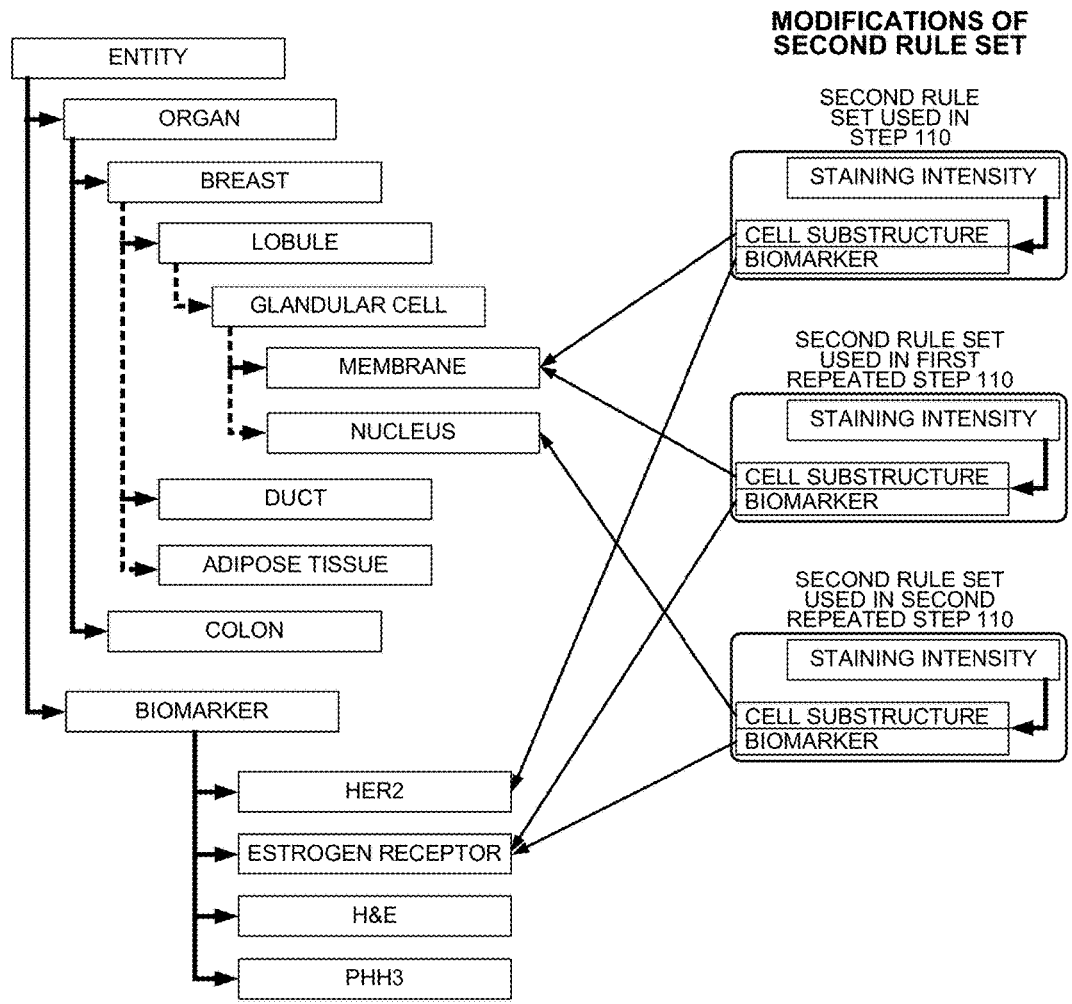
FIG. 31 is a diagram illustrating how the topology of FIG. 30 is used to modify a rule set that is used to measure a characteristic of image objects.

FIG. 31 illustrates how topology 142 is used to modify the second rule set that is used in step 110 to measure the first characteristic of the first objects. The first time step 110 is performed, the second rule set measured the characteristic "staining intensity," defined as the intensity by which the biomarker HER2 stained the membranes of glandular cells. In step 115, system 100 determines the correlation between the resulting second numerical data and the clinical data for the patient. Then in step 116, the second rule set is modified to measure the intensity by which the estrogen receptor stained the membranes of glandular cells, and step 110 is repeated. Step 115 is repeated, and the correlation between the second numerical data and the clinical data for the patient is again determined. Even if the correlation is improved, the second rule set is modified again to measure the intensity by which the estrogen receptor stained the nucleus of glandular cells, and step 110 is repeated again. The correlation is also determined for the second modification of the second rule set. Method 118 then defines the second rule set based on the combination of biomarker and stained cell substructure that resulted in the best correlation between the second numerical data generated in step 114 and the clinical data for the patient.

By modifying the rule sets according to the structure of an ontology based on expert knowledge, the correlation between the second numerical data and the actual clinical data of the patient can be improved in a systematic manner while permitting the modification step 116 to be repeated the fewest number of times. In order to reduce the number of repetitions of step 116 required to achieve a desired correlation, a "genetic algorithm" can be used to eliminate those first characteristics of the first objects that will not likely lead to an improved correlation.

Figure 32:
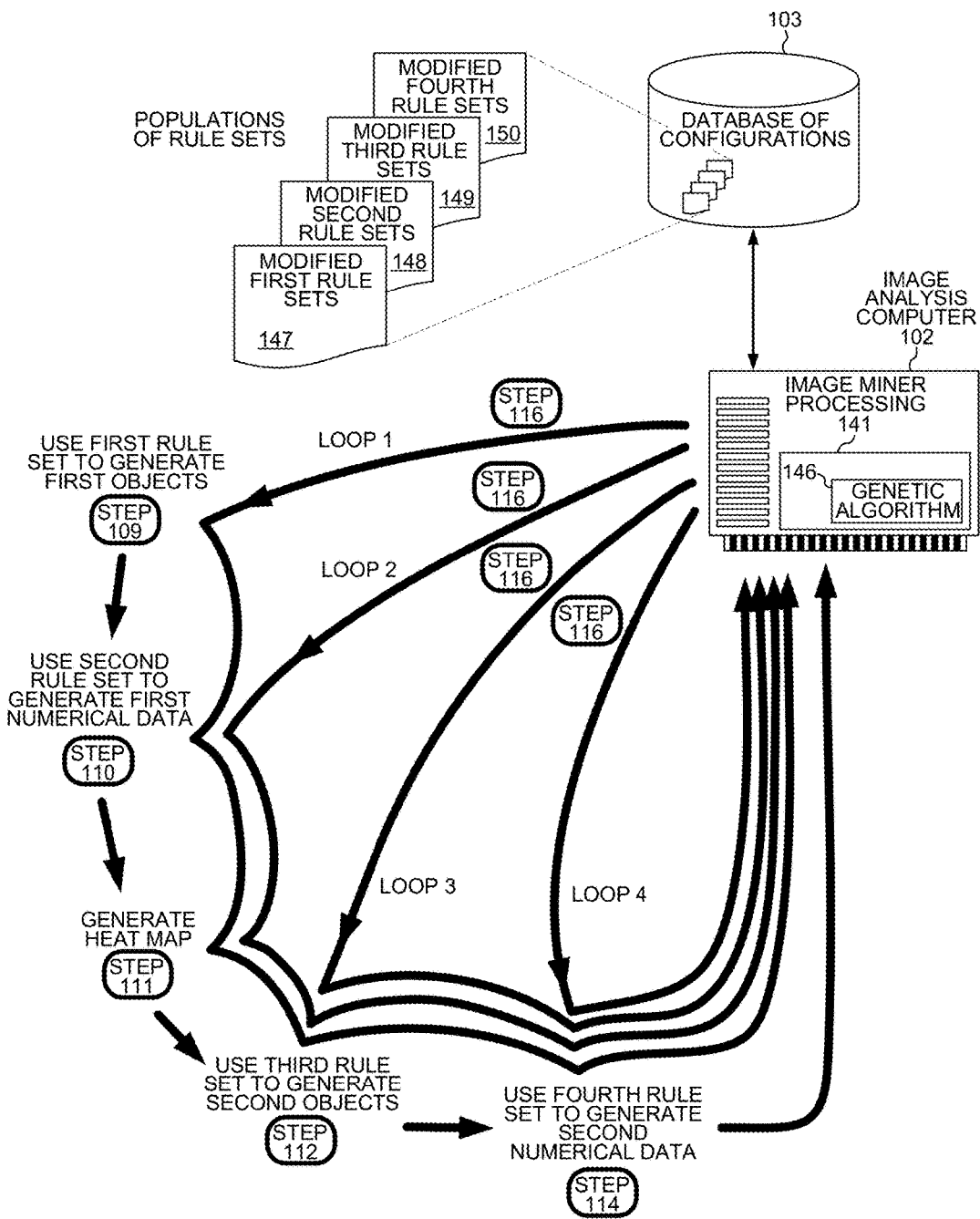
FIG. 32 illustrates the steps for improving the correlation between generated numerical data and actual clinical data of patients by using a genetic algorithm to improve and limit the populations of modified rule sets.

FIG. 32 illustrates a genetic algorithm 146 that is used to select the best first, second, third and fourth rule sets 147-150 by weeding out modified rule sets and their associated characteristics that are less likely to improve the correlation in step 116. Genetic algorithm 146 is executed by the image miner processor 141, and the populations of promising modified rule sets 147-150 are stored in the database 103 of configurations. For example, as the steps of loop 2 are performed, modified second rule sets are selected that no longer measure those characteristics that have been eliminated by the genetic algorithm 146. The genetic algorithm mimics the process of natural selection and uses "evolution" to determine the best second rule set from among the population 148 of second rule sets that results in the second numerical data with the best correlation to the actual clinical data. Genetic algorithm 146 is used not only to improve the selection of modified second rule sets 148 but also to improve the populations of modified first, third and fourth rule sets.

The "mutation" (modification) of the second rule sets of population 148 occurs based on the structure of the ontology and on the image objects actually found in the tiles obtained from tissue slices. Ontology 142 combines a class network describing possible classes of image objects with an ontology of possible characteristics for those objects. After the segmentation step 109 and the data analysis step 110 are performed, the image objects that fall within each of the object classes and subclasses are known. If a type of class or subclass is not detected on a tile, then the characteristics that describe the missing class or subclass are not used, and the ontology is revised. The revision of the ontology affects the topological distances used to determine the iterative modifications of the rule sets. The ontology 142 is also structured using expert knowledge regarding which characteristics are most likely to result in a correlation between actual clinical outcomes and image and data analysis results. The most useful characteristics are given higher topological positions.

Although the present invention has been described in connection with certain specific embodiments for instructional purposes, the present invention is not limited thereto. Although method 118 is described as modifying rule sets in order to improve the correlation between actual clinical outcomes and predicted outcomes of human patients, the method can also be used to generate image-based diagnostic tests by improving the correlation between actual outcomes and predicted outcomes of animal models of human patients by analyzing images of tissue samples of the laboratory animals. Accordingly, various modifications, adaptations, and combinations of various features of the described embodiments can be practiced without departing from the scope of the invention as set forth in the claims.

What is claimed is:

1. A method comprising:
    (a) generating first objects that are linked to pixels of a digital image of a slice of tissue of a patient, wherein a first rule set defines which pixels are linked to the first objects;
    (b) using a second rule set to generate a first numerical image layer by measuring a first characteristic of the first objects, wherein each pixel of the first numerical image layer has a value proportional to the first characteristic of the first object linked to that pixel;
    (c) generating a heat map by downscaling the first numerical image layer;
    (d) generating second objects from the heat map, wherein a third rule set defines which pixels of the heat map are linked to each of the second objects;
    (e) using a fourth rule set to generate numerical data by measuring a second characteristic of the second objects detected in the heat map;
    (f) determining how well the numerical data correlates with clinical data for the patient;
    (g) improving how well the numerical data correlates with the clinical data for the patient by modifying the first rule set, the second rule set, the third rule set and the fourth rule set and then repeating (b) through (e); and
    (h) defining an image-based diagnostic test based on the first rule set, the second rule set, the third rule set and the fourth rule set.

2. The method of claim 1, wherein the first objects and the pixels linked to the first objects are part of a data network.

3. The method of claim 1, wherein the patient is an animal model of a human patient.

4. The method of claim 1, wherein the first characteristic and the second characteristic are listed in an ontology, and wherein the fourth rule set is modified in (g) based on a topological distance in the ontology between the first characteristic and the second characteristic.

5. The method of claim 1, wherein the slice of tissue of the patient is stained with a biomarker taken from the group consisting of: hematoxylin and eosin (H&E), phosphohistone H3 (PHH3) mitotic marker, Human Epidermal growth factor Receptor 2 (HER2) membrane stain, cytokeratin 18 (CK18) cytoplasmic stain, cell proliferation marker Ki67, estrogen receptor (ER) stain, progesterone receptor (PR) stain, and cluster of differentiation (CD) 3 stain, CD 8 stain, CD 23 stain and CD 44 stain.

6. The method of claim 1, further comprising:
(i) displaying the heat map and the second objects on a graphical user interface.

7. The method of claim 1, wherein the first rule set, the second rule set, the third rule set and the fourth rule are modified in (g) in a manner that reduces computational resources required to repeat (a) through (f).

8. The method of claim 1, wherein the image-based diagnostic test predicts a probability that the patient will remain disease free for a predetermined period of time after a clinical action on the patient.

9. The method of claim 1, wherein the slice of tissue is immunohistochemically stained for the expression of a protein.

10. The method of claim 1, wherein the numerical data includes a mean pixel intensity value of a group of second objects detected in the heat map.

11. The method of claim 1, wherein the numerical data correlates well with the clinical data for the patient when a survival time of the patient predicted by the image-based diagnostic test equals an actual survival time of the patient.

12. The method of claim 1, wherein the image-based diagnostic test predicts a probability of recurrence of cancer.

13. A method comprising:
(a) generating first objects that are linked to pixels of a higher resolution digital image of a tissue slice of a patient, wherein a first rule set defines which higher resolution pixels are linked to which of the first objects;
(b) using a second rule set to generate a lower resolution digital image comprising heat map pixels, wherein a subset of the heat map pixels have locations on the lower resolution digital image corresponding to where an associated first object is located on the higher resolution digital image, and wherein each of the heat map pixels in the subset has a value corresponding to a first characteristic of the first objects;
(c) generating second objects from the lower resolution digital image, wherein a third rule set defines which heat map pixels are linked to each of the second objects;
(d) using a fourth rule set to generate numerical data by measuring a second characteristic of the second objects detected in the lower resolution digital image;
(e) determining how well the numerical data correlates with clinical data for the patient;
(f) improving how well the numerical data correlates with the clinical data for the patient by modifying the second rule set, the third rule set and the fourth rule set and then repeating (b) through (e); and
(g) defining an image-based diagnostic test based on the second rule set, the third rule set and the fourth rule set.

14. The method of claim 13, further comprising:
(h) displaying the lower resolution digital image on a graphical user interface.

15. The method of claim 13, wherein each of the heat map pixels has a color dependent on information obtained by analyzing both the first objects and the second objects.

16. The method of claim 13, wherein the numerical data correlates well with the clinical data for the patient when a survival time of the patient predicted by the image-based diagnostic test equals an actual survival time of the patient.

17. The method of claim 13, wherein the image-based diagnostic test predicts a probability that prostate cancer will recur in the patient, and wherein the tissue slice is stained with a biomarker that stains basal cells.

18. The method of claim 13, wherein the image-based diagnostic test predicts whether the patient belongs to a short-lived group of patients or to a long-lived group of patients, and wherein the tissue slice is stained with a protein specific antibody that stains immune cells.

19. The method of claim 13, wherein the first characteristic and the second characteristic are listed in an ontology, and wherein the fourth rule set is modified in (f) based on a topological distance in the ontology between the first characteristic and the second characteristic.

20. A method comprising:
(a) generating objects that are linked to pixels of a higher resolution digital image of a tissue slice of a patient and that a classified as belonging to a first class, wherein a first rule set defines which higher resolution pixels are linked to which of the objects and which objects are classified as belonging to the first class;
(b) using a second rule set to generate a lower resolution digital image comprising heat map pixels, wherein each heat map pixel corresponds to a region on the higher resolution digital image, and wherein each heat map pixel has a value corresponding to how many objects belong to the first class within the region;
(c) generating second objects from the lower resolution digital image, wherein a third rule set defines which heat map pixels are linked to each of the second objects;
(d) using a fourth rule set to generate numerical data by measuring a second characteristic of the second objects detected in the lower resolution digital image;
(e) determining how well the numerical data correlates with clinical data for the patient;
(f) improving how well the numerical data correlates with the clinical data for the patient by modifying the second rule set, the third rule set and the fourth rule set and then repeating (b) through (e); and
(g) defining an image-based diagnostic test based on the second rule set, the third rule set and the fourth rule set.

* * * * *

UNITED STATES PATENT AND TRADEMARK OFFICE
CERTIFICATE OF CORRECTION

PATENT NO. : 9,741,112 B2  
APPLICATION NO. : 14/850436  
DATED : August 22, 2017  
INVENTOR(S) : Schoenmeyer et al.

Page 1 of 1

It is certified that error appears in the above-identified patent and that said Letters Patent is hereby corrected as shown below:

In the Claims

Column 29, Line 5, the words "fourth rule are" should be changed to --fourth rule set are--.

Column 30, Line 28, the words "that a classified" should be changed to --that are classified--.

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*